(12) United States Patent
Dyker et al.

(10) Patent No.: US 6,414,158 B1
(45) Date of Patent: Jul. 2, 2002

(54) 1,3,4-OXADIAZINE DERIVATIVES AND THEIR USE AS PESTICIDES

(75) Inventors: Hubert Dyker, Köln; Andrew Plant, Leverkusen; Jürgen Scherkenbeck, Wermelskirchen; Christoph Erdelen, Leichlingen; Achim Harder, Köln, all of (DE)

(73) Assignee: Bayer AKtiengesellschaft, Leverkusen (DE)

( * ) Notice: Subject to any disclaimer, the term of this patent is extended or adjusted under 35 U.S.C. 154(b) by 0 days.

(21) Appl. No.: 09/610,794

(22) Filed: Jul. 6, 2000

Related U.S. Application Data

(62) Division of application No. 09/142,982, filed as application No. PCT/EP97/01325 on Mar. 17, 1997, now Pat. No. 6,127,364.

(30) Foreign Application Priority Data

Mar. 29, 1996  (DE) .......................................... 196 12 644

(51) Int. Cl.[7] ............................................. C07C 281/02
(52) U.S. Cl. .................. 546/332; 548/507; 549/76; 549/452; 558/233; 560/24; 560/30; 560/31; 560/32; 560/115; 560/159
(58) Field of Search ............................ 558/233; 560/24, 560/30, 31, 32, 115, 159; 546/332; 548/507; 549/76, 452

(56) References Cited

U.S. PATENT DOCUMENTS

| 4,064,236 A | 12/1977 | Dorn et al. | 424/177 |
|---|---|---|---|
| 4,670,555 A | 6/1987 | Dekeyser | 544/68 |

FOREIGN PATENT DOCUMENTS

| DE | 3627161 | 2/1987 |
|---|---|---|

OTHER PUBLICATIONS

Leibigs Ann. Chem. (month unavailable) 1981, pp. 1433–1444, Fahr et al, Azomethin–imine Durch Umsetzung von Diphenylketen mit Azodicarbonsäureestern.

J. Chem. Soc. Perkins Trans. I, (month unavailable) 1975, pp. 1712–1720, Dutta et al, Polypeptides. Part XIII. Preparation of a–Aza–amino–acid (Carbazic Acid) Derivatives and Intermediates for the Preparation of a–Aza–peptides.

Org. Syntheses Coll., vol. 5, (month unavailable) 1973, pp. 201–204, Staab et al 1,1'–Carbonyldiimidazole.

Tetrahedron Letters, vol. 28, No. 17, (month unavailable) 1987, pp. 1873–1876, Konz et al, Stereocontrolled Synthesis of D–a–Hydroxy Carboxylic Acids from L–Amino Acids.

Tetrahedron Letters, vol. 26, No. 43, (month unavailable) 1985, pp. 5257–5260, Lerchen et al Stereoselektive Synthese von D–a–Hydroxycarbonsäuren BZW. D–a–Hydroxycarbonsäuren Enthaltenden Depsipeptiden Aus L–Aminosäuren.

Compr. Org. Chem. vol. 2, (month unavailable) 1979, pp. 739–778, S.M. Roberts, Hydroxy and Alkoxy Carboxylic Acids.

Ullmanns Ency. Techn. Chem. $4^{th}$ edition (month unavailable) 1977, vol. 13, p. 163, Sunmdermann et al, Hydroxycarbonsäuren, aromatishe.

J. Am. Chem. Soc. 76, Jul. 26, 1954, Fu et al, pp. 6054–6058, Influence of Optically Active Acyl Groups on the Enzymatic Hydrolysis of N–Acylated–L–amino Acids.

Advances in Protein Chemistry, vol. IV, Anson, Edsall (Eds), (month unavailable, 1948, p. 33, Protein Gels.

Il Farmaco, 50 (6) (month unavailable) 1995, Jacqueline Marchand–Brynaert et al, pp. 455–4 Design, Synthesis and Evaluation of D,D–Peptidase and Beta–Lactamase Inhibitors: Azapeptide Oxapeptides and Related Heterocycles.

Chemia Analityczna, Warszawa, vol. 17, No. 2, (month unavailable) 1972, pp. 379–385, Jonoforeza Bibulowa Ketonow I Aldehydow W. Postaci Ksanthydrazonow, Stanislow Plaza.

*Primary Examiner*—Richard L. Raymond
(74) *Attorney, Agent, or Firm*—Joseph C. Gil; Raymond J. Harmuth

(57) ABSTRACT

The invention relates to novel carbazate intermediates of formula (II), and to a process for their preparation, and their usefulness in the preparation of (1,3,4) oxadiazine derivatives useful as pesticides, in particular as anthelminthicides, insecticides, acaricides, and nematicides.

6 Claims, No Drawings

1,3,4-OXADIAZINE DERIVATIVES AND THEIR USE AS PESTICIDES

This application is a divisional of U.S. Ser. No. 09/142,982, filed on Sep. 18, 1998, now U.S. Pat. No. 6,127,364, which is a 371 of PCT/EP97/01325, filed Mar. 17, 1997.

The invention relates to novel (1,3,4)-oxadiazine derivatives, to a plurality of processes and intermediates for their preparation and to their use as pesticides, in particular as anthelmintics, insecticides, acaricides and nematicides.

Only a single representative of the 2,5-dichalkogeno-(1,3,4)-oxadiazinanes, 6,6-diphenyl-(1,3,4)-oxadiazinane-2,5-dione is hitherto known (Liebigs Ann. Chem. 1981, 1433).

This invention, accordingly, provides novel (1,3,4)-oxadiazine derivatives of the formula (I)

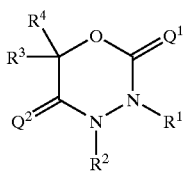

(I)

in which $R^1$ and $R^2$ independently of one another each represent hydrogen, respectively, optionally halogen-substituted alkyl, hydroxyalkyl, alkanoyloxyalkyl, alkoxyalkyl, arylalkoxyalkyl, mercaptoalkyl, alkylthioalkyl, alkylsulphinylalkyl, alkylsulphonylalkyl, carboxyalkyl, alkoxycarbonylalkyl, aryloxycarbonylalkyl, arylalkyloxycarbonylalkyl, carbamoylalkyl, aminoalkyl, alkylaminoalkyl, dialkylaminoalkyl, alkoxycarbonylaminoalkyl, alkylcarbonyl, cycloalkylcarbollyl or represent respectively optionally substituted cycloalkyl, cycloalkylalkyl, aryl, arylalkyl, arylcarbonyl, heterocyclylalkyl, hetaryl or hetarylalkyl or $R^1$, $R^2$ and the two linking nitrogen atoms represent an optionally substituted heterocyclic ring, $R^3$ and $R^4$ independently of one another each represent hydrogen, respectively optionally halogen-substituted alkyl, alkenyl, hydroxyalkyl, alkanoyloxyalkyl, alkoxyalkyl, arylalkoxyalkyl, mercaptoalkyl, alkylthioalkyl, alkylsulphinylalkyl, alkylsulphonylalkyl, alkoxycarbonylalkyl, aryloxycarbonylalkyl, arylalkyloxycarbonylalkyl, carbamoylalkyl, aminoalkyl, alkylaminoalkyl, dialkylaminoalkyl, alkylcarbonyl, cycloalkylcarbonyl or represent respectively optionally substituted cycloalkyl, cycloalkylalkyl, aryl, arylalkyl, hetaryl or hetarylalkyl or $R^3$ and $R^4$ together represent alkylene or the radical (a)

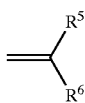

(a)

in which $R^5$ and $R^6$ independently of one another each represent hydrogen, respectively optionally halogen-substituted alkyl, alkenyl, hydroxyalkyl, alkanoyloxyalkyl, alkoxy alkyl, arylalkoxyalkyl, mercaptoalkyl, alkylthioalkyl, alkylsulphinylalkyl, alkylsulphonylalkyl, alkoxycarbonylalkyl, aryloxycarbonylalkyl, aminoalkyl, alkylaminoalkyl, dialkylaminoalkyl, alkylcarbonyl or represent respectively optionally substituted cycloalkyl, cycloalkylalkyl, aryl, arylalkyl, hetaryl or hetarylalkyl and $Q^1$ and $Q^2$ independently of one another each represent oxygen or sulphur, except for 6,6-diphenyl-(1,3,4)-oxadiazinane-2,5-dione.

Depending inter alia on the nature of the substituents, the compounds of the formula (I) may be present as geometric and/or optical isomers or mixtures of isomers, in varying compositions, which can, if appropriate, be separated in a customary manner. The present invention provides both the pure isomers and the isomer mixtures, their preparation and their use and compositions comprising them. Hereinbelow, for the sake of simplicity, reference is however always made to compounds of the formula (I) although this includes both the pure isomers and, if appropriate, also mixtures having varying proportions of isomeric compounds.

Furthermore, it has been found that the novel compounds of the formula (I) are obtained by one of the processes described below.

A) (1,3,4)-Oxadiazine derivatives of the formula (I-a)

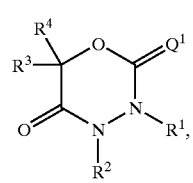

(I-a)

in which $R^1$ to $R^4$ and $Q^1$ are each as defined above, can be prepared by reacting carbazates of the formula (II)

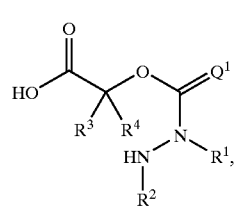

(II)

in which $R^1$ to $R^4$ and $Q^1$ are each as defined above, in the presence of a reaction auxiliary and a diluent and, if appropriate, in the presence of a base.

B) (1,3,4)-Oxadiazine derivatives of the formula (I-b)

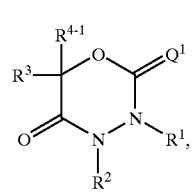

(I-b)

in which $R^1$ to $R^3$, $Q^1$ and $Q^2$ are each as defined above and $R^{4-1}$ represents the same radicals as $R^4$, with the exception of hydrogen, can be prepared by reacting
(1,3,4)-oxadiazine derivatives of the formula (I-c)

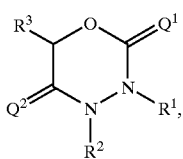
(I-c)

in which
R¹ and R² have meanings other than hydrogen,
R³, Q¹ and Q² are each as defined above,
with compounds of the formula (III)

R⁴⁻¹-E    (III), in which
R⁴⁻¹ is as defined above and
E represents an electron-withdrawing leaving group,
if appropriate in the presence of a diluent and, if appropriate, in the presence of a reaction auxiliary.

C) (1,3,4)-Oxadiazine derivatives of the formula (I-d)

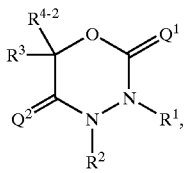
(I-d)

in which
R¹ to R³, Q¹ and Q² are each as defined above and
R⁴⁻² represents the radical (b)

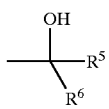
(b)

in which
R⁵ and R⁶ independently of one another each represent hydrogen, optionally substituted alkyl or aryl, or
R³ and R⁴⁻² together represent the radical (a)

(a)

in which
R⁵ and R⁶ are each as defined above, can be prepared by reacting
(1,3,4)-oxadiazine derivatives of the formula (I-c)

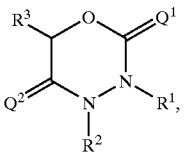
(I-c)

in which
R¹ to R³, Q¹ and Q² are each as defined above
with ketones or aldehydes of the formula (IV)

R⁵—CO—R⁶    (IV), in which
R⁵ and R⁶ are each as defined above,
if appropriate in the presence of a diluent and, if appropriate, in the presence of a reaction auxiliary, and subsequently, if appropriate, eliminating water.

D) (1,3,4)-Oxadiazine derivatives of the formula (I-e)

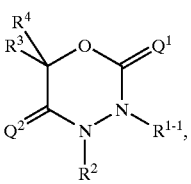
(I-e)

in which
R¹⁻¹ represents the same radicals as R¹, with the exception of hydrogen,
R² to R⁴, Q¹ and Q² are each as defined above,
can be prepared by reacting (1,3,4)-oxadiazine derivatives of the formula (I-f)

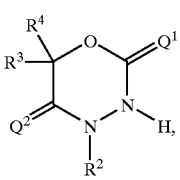
(I-f)

in which
R² to R⁴, Q¹ and Q² are each as defined above,
with compounds of the formula (V)

R¹⁻¹-E    (V), in which
R¹⁻¹ is as defined above and
E represents an electron-withdrawing leaving group,
if appropriate in the presence of a diluent and, if appropriate, in the presence of a reaction auxiliary.

E) (1,3,4)-Oxadiazine derivatives of the formula (I-g)

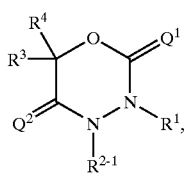

(I-g)

in which
R$^1$, R$^3$, R$^4$, Q$^1$ and Q$^2$ are each as defined above and
R$^{2-1}$ represents the same radicals as R$^2$, with the exception of hydrogen,
can be prepared by reacting (1,3,4)-oxadiazine derivatives of the formula (I-h)

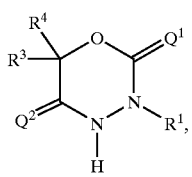

(I-h)

in which
R$^1$ R$^3$, R$^4$, Q$^1$ and Q$^2$ are each as defined above,
with compounds of the formula (VI)

R$^{2-1}$-E    (VI), in which
R$^{2-1}$ is as defined above and
E represents an electron-withdrawing leaving group,
if appropriate in the presence of a diluent and, if appropriate, in the presence of a reaction auxiliary.

F) (1,3,4)-Oxadiazine derivatives of the formula (I)

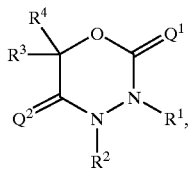

(I)

in which
R$^1$ to R$^4$, Q$^1$ and Q$^2$ are each as defined above,
can be prepared by reacting and cyclocondensing compounds of the formula (VII)

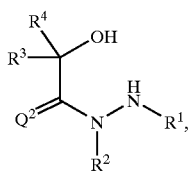

(VII)

in which
R$^1$ to R$^4$ and Q$^2$ are each as defined above, with compounds of the formula (VIII)

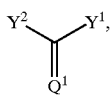

(VIII)

in which
Y$^1$ represents chlorine, trichloromethoxy, C$_1$–C$_4$-alkoxy, optionally substituted phenoxy, 1-imidazolyl or 1,2,4-triazolyl and
Y$^2$ represents chlorine, trichloromethoxy, 1-imidazolyl or 1,2,4-triazolyl,
Q$^1$ is as defined above,
if appropriate in the presence of a diluent and, if appropriate, in the presence of a reaction auxiliary.

G) (1,3,4)-Oxadiazine derivatives of the formula (I)

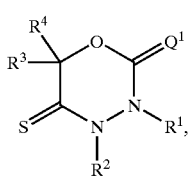

(I)

in which
R$^1$ to R$^4$, Q$^1$ and Q$^2$ are each as defined above,
can be prepared by cyclocondensing compounds of the formula (IX)

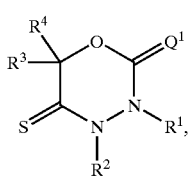

(IX)

in which
R$^1$ to R$^4$, Q$^1$, Q$^2$ and Y$^1$ are each as defined above,
if appropriate in the presence of a diluent and, if appropriate, in the presence of a reaction auxiliary.

H) (1,3,4)-Oxadiazine derivatives of the formula (I-i)

(I-i)

in which
R$^1$ to R$^4$ and Q$^1$ are each as defined above,
can be prepared by reacting (1,3,4)-oxadiazine derivatives of the formula (I-a)

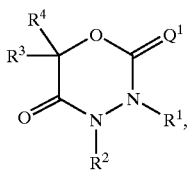

(I-a)

in which
R$^1$ to R$^4$ and Q are each as defined above,
with a thionylating reagent, if appropriate in the presence of a diluent.

Furthermore, it has been found that the novel compounds of the formula (I) have very high activity as pesticides, preferably for controlling endoparasites in useful animals and for controlling insects, arachnids and nematodes encountered in agriculture, in forests, in the protection of stored products and materials and in the hygiene sector.

The formula (I) provides a general definition of the compounds according to the invention. Preferred substituents and ranges of the radicals listed in the formulae mentioned hereinabove and hereinbelow are illustrated below.

R$^1$ and R$^2$ independently of one another each preferably represent hydrogen, C$_1$–C$_{15}$-alkyl, in particular also 3,7,11-trimethyldodecyl, represent respectively optionally fluorine-, chlorine- or bromine-substituted C$_1$–C$_8$-alkyl, C$_3$–C$_7$-cycloalkyl, C$_3$–C$_7$-cycloalkyl-C$_1$–C$_4$-alkyl, C$_1$–C$_6$-hydroxyalkyl, C$_1$–C$_4$-alkanoyloxy-C$_1$–C$_6$-alkyl, C$_1$–C$_4$-alkoxy-C$_1$–C$_6$-alkyl, aryl-C$_1$–C$_4$-alkoxy-C$_1$–C$_6$-alkyl, C$_1$–C$_6$-mercaptoalkyl, in particular mercaptomethyl, C$_1$–C$_4$-alkylthio-C$_1$–C$_6$-alkyl, in particular methylthioethyl, C$_1$–C$_4$-alkylsulphinyl-C$_1$–C$_6$-alkyl, in particular methylsulphinylethyl, C$_1$–C$_4$-alkylsulphonyl-C$_1$–C$_6$-alkyl, in particular methylsulphonylethyl, carboxy-C$_1$–C$_6$-alkyl, in particular carboxymethyl or carboxyethyl, C$_1$–C$_4$-alkoxycarbonyl-C$_1$–C$_6$-alkyl, in particular methoxycarbonylmethyl or ethoxycarbonylethyl, aryloxycarbonyl-C$_1$–C$_6$-alkyl, in particular phenoxycarbonylmethyl, aryl-C$_1$–C$_4$-alkyloxycarbonyl-C$_1$–C$_6$-alkyl, in particular benzyloxycarbonylmethyl, carbamoyl-C$_1$–C$_6$-alkyl, in particular carbamoylmethyl or carbamoylethyl, amino-C$_1$–C$_6$-alkyl, in particular aminopropyl or aminobutyl, C$_1$–C$_4$-alkylamino-C$_1$–C$_6$-alkyl in particular methylaminopropyl or methylamino, di-(C$_1$–C$_4$)-alkylamino-C$_1$–C$_6$-alkyl in particular dimethylaminopropyl or dimethylaminobutyl, C$_1$–C$_4$-alkoxycarbonylamino-C$_1$–C$_6$-alkyl, C$_1$–C$_6$-alkylcarbonyl, C$_3$–C$_7$-cycloalkylcarbonyl or represent aryl, aryl-C$_1$–C$_4$-alkyl, arylcarbonyl, aryl-C$_1$–C$_4$-alkylcarbonyl, hetaryl or hetaryl-C$_1$–C$_4$-alkyl, where optionally one NH function in the heterocyclic ring may be derivatized by an amino protective group such as, for example, those mentioned above, each of which is optionally substituted by halogen, hydroxyl, nitro, cyano, amino, C$_1$–C$_4$-alkylamino, di-(C$_1$–C$_4$)-alkylamino, benzylamino, dibenzylamino, protected amino such as, for example, acetyl-, t-butoxycarbonyl-, benzyloxycarbonyl- or FMOC-amino, C$_1$–C$_6$-alkyl, C$_1$–C$_4$-halogenoalkyl, C$_1$–C$_4$-alkoxy or C$_1$–C$_4$-halogenoalkoxy. and optionally C$_1$–C$_4$-alkyl-substituted heterocyclyl-C$_1$–C$_4$-alkyl such as, for example, dioxolanylmethyl.

R$^1$ and R$^2$ together with the two linking nitrogen atoms preferably represent an optionally halogen-, hydroxyl-, nitro-, cyano-, C$_1$–C$_4$-alkyl-, C$_1$–C$_4$-halogenoalkyl-, C$_1$–C$_4$-alkoxy- or C$_1$–C$_4$-halogenoalkoxy-substituted 5- to 8-membered saturated or unsaturated heterocyclic ring.

R$^3$ and R$^4$ independently of one another each preferably represent hydrogen, C$_1$–C$_{16}$-alkyl, represent respectively optionally fluorine-, chlorine- or bromine-substituted C$_1$–C$_6$-alkyl, C$_2$–C$_8$-alkenyl, C$_3$–C$_7$-cycloalkyl, C$_3$–C$_7$-cycloalkyl-C$_1$–C$_4$-alkyl, C$_1$–C$_6$-hydroxyalkyl, C$_1$–C$_4$-alkanoyloxy-C$_1$–C$_6$-alkyl in particular acetoxymethyl or 1-acetoxyethyl, C$_1$–C$_4$-alkoxy-C$_1$–C$_6$-alkyl in particular methoxymethyl or 1-methoxyethyl, aryl-C$_1$–C$_4$-alkoxy-C$_1$–C$_6$-alkyl, C$_1$–C$_6$-mercaptoalkyl, in particular mercaptomethyl, C$_1$–C$_4$-alkylthio-C$_1$–C$_6$-alkyl, in particular methylthioethyl, C$_1$–C$_4$-alkylsulphinyl-C$_1$–C$_6$-alkyl, in particular methylsulphinylethyl, C$_1$–C$_4$-alkylsulphonyl-C$_1$–C$_6$-alkyl, in particular methylsulphonylethyl, C$_1$–C$_4$-alkoxycarbonyl-C$_1$–C$_6$-alkyl, aryloxycarbonyl-C$_1$–C$_6$-alkyl, in particular phenoxycarbonylmethyl, aryl-C$_1$–C$_4$-alkyloxycarbonyl-C$_1$–C$_6$-alkyl, carbamoyl-C$_1$–C$_6$-alkyl, in particular carbamoylmethyl or carbamoylethyl, amino-C$_1$–C$_6$-alkyl, C$_1$–C$_4$-alkylamino-C$_1$–C$_6$-alkyl, di-C$_1$–C$_4$-alkylamino-C$_1$–C$_6$-alkyl, C$_1$–C$_6$-alkylcarbonyl, C$_3$–C$_7$-cycloalkylcarbonyl, or represent aryl, aryl-C$_1$–C$_4$-alkyl, arylcarbonyl, hetaryl or hetaryl-C$_1$–C$_4$-alkyl, each of which is optionally substituted by halogen, hydroxyl, cyano, C$_1$–C$_6$-alkyl, C$_1$–C$_4$-halogenoalkyl, C$_1$–C$_4$-alkoxy, C$_1$–C$_4$-halogenoalkoxy, benzyloxy or silyloxy which is trisubstituted by C$_1$–C$_4$-alkyl and/or phenyl.

R$^3$ and R$^4$ together preferable represent C$_2$–C$_7$-alkylene or the radical (a)

(a)

in which
R$^5$ and R$^6$ independently of one another each represent hydrogen, respectively optionally fluorine-, chlorine- or bromine-substituted C$_1$–C$_6$-alkyl, C$_2$–C$_4$-1-alkenyl or C$_3$–C$_7$-cycloalkyl or represent respectively optionally halogen-, hydroxyl-, nitro-, C$_1$–C$_6$-alkyl-, C$_1$–C$_4$-halogenoalkyl-, C$_1$–C$_4$-alkoxy-, C$_1$–C$_4$-halogenoalkoxy-, phenoxy-, amino-, C$_1$–C$_4$-alkylamino- or di-(C$_1$–C$_4$)-alkylamino-substituted phenyl, phenyl-C$_1$–C$_4$-alkyl or 5- or 6-membered hetaryl.

Q$^1$ and Q$^2$ independently of one another each preferably represent oxygen or sulphur.

6,6-Diphenyl-(1,3,4)-oxadiazinane-2,5-dione is excluded from the preferred range.

R$^1$ and R$^2$ independently of one another each particularly preferably represent hydrogen, C$_1$–C$_{10}$-alkyl, represent respectively optionally fluorine-, chlorine- or bromine-substituted C$_1$–C$_4$-alkyl, C$_3$–C$_7$-cycloalkyl, in particular cyclopentyl, cyclohexyl or cycloheptyl, C$_3$–C$_7$-cycloalkyl-C$_1$–C$_4$-alkyl, C$_1$–C$_6$-hydroxyalkyl, in particular hydroxymethyl or 1-hydroxyethyl, C$_1$–C$_4$-alkanoyloxy-C$_1$–C$_6$-alkyl, in particular acetoxymethyl or 1-acetoxyethyl, C$_1$–C$_4$-alkoxy-C$_1$–C$_6$-alkyl, in particular methoxymethyl or 1-methoxyethyl, phenyl-C$_1$–C$_4$-alkoxy-C$_1$–C$_6$-alkyl, in particular benzyloxymethyl or 1-benzyloxyethyl, C$_1$–C$_4$-alkoxycarbonylamino-C$_1$–C$_6$-alkyl, in particular tert-butoxycarbonylaminopropyl or tert-butoxycarbonylaminobutyl, C$_1$–C$_6$-alkylcarbonyl, in particular acetyl, propionyl or butyryl, C$_3$–C$_7$-cycloalkylcarbonyl, in particular cyclopropylcarbonyl or cyclohexylcarbonyl, or represent phenyl, phenyl-C$_1$–C$_4$-alkyl, phenylcarbonyl, 5- or 6-membered hetaryl, in particular thienyl, thiazolyl or pyridyl, 5- or 6-membered hetaryl-C$_1$–C$_4$-alkyl or indolyl-C$_1$–C$_4$-alkyl, each of which is optionally substituted by fluorine, chlorine, bromine, iodine, hydroxyl, nitro, cyano, amino, $C_1$–$C_4$-alkylamino, di-($C_1$–$C_4$)-alkylamino, benzylamino, dibenzylamino, protected amino such as, for example, acetyl-, t-butoxycarbonyl-, benzyloxycarbonyl- or FMOC-amino, $C_1$–$C_4$-alkyl, $C_1$–$C_4$-halogenoalkyl, $C_1$–$C_4$-alkoxy or $C_1$–$C_2$-halogenoalkoxy.

$R^1$ and $R^2$ together with the two linking nitrogen atoms particularly preferably represent an optionally fluorine-, chlorine-, bromine-, hydroxyl-, nitro-, cyano-, $C_1$–$C_4$-alkyl-, $C_1$–$C_4$-halogenoalkyl-, $C_1$–$C_4$-alkoxy- or $C_1$–$C_2$-halogenoalkoxy-substituted 5- to 8-membered saturated or unsaturated heterocyclic ring.

$R^3$ and $R^4$ independently of one another each particularly preferably represent hydrogen, $C_1$–$C_{12}$-alkyl, represent respectively optionally fluorine-, chlorine- or bromine-substituted $C_1$–$C_4$-alkyl, $C_2$–$C_6$-alkenyl, $C_3$–$C_7$-cycloalkyl, in particular cyclopentyl, cyclohexyl or cycloheptyl, $C_3$–$C_7$-cycloalkyl-$C_1$–$C_4$-alkyl, $C_1$–$C_6$-hydroxyalkyl, phenyl-$C_1$–$C_4$-alkoxy-$C_1$–$C_6$-alkyl, in particular benzyloxymethyl or 1-benzyloxyethyl, $C_1$–$C_4$-alkylthio-$C_1$–$C_6$-alkyl, in particular methylthioethyl, $C_1$–$C_4$-alkoxycarbonyl-$C_1$–$C_6$-alkyl, in particular methoxycarbonylmethyl or ethoxycarbonylethyl, phenyl-$C_1$–$C_4$-alkyloxycarbonyl-$C_1$–$C_6$-alkyl, in particular benzyloxycarbonylmethyl, amino-$C_1$–$C_6$-alkyl, in particular aminopropyl or aminobutyl, $C_1$–$C_4$-alkylamino-$C_1$–$C_6$-alkyl, in particular methylaminopropyl or methylaminobutyl, di-($C_1$–$C_4$)-alkylamino-$C_1$–$C_6$-alkyl, in particular dimethylaminopropyl or dimethylaminobutyl, $C_1$–$C_6$-alkylcarbonyl, in particular acetyl, propionyl or butyryl, $C_3$–$C_7$-cycloalkylcarbonyl, in particular cyclopropylcarbonyl or cyclohexylcarbonyl or represent phenyl, phenyl-$C_1$–$C_4$-alkyl, naphthylmethyl, phenylcarbonyl, 5- or 6-membered hetaryl, in particular thienyl, thiazolyl or pyridyl, indolyl, benzo-1,3-dioxolyl, 5- or 6-membered hetaryl-$C_1$–$C_4$-alkyl in particular thienylmethyl, thiazolylmethyl, imidazolylmethyl or pyridylmethyl or indolyl-$C_1$–$C_4$-alkyl, each of which is optionally substituted by fluorine, chlorine, bromine, iodine, hydroxyl, cyano, $C_1$–$C_6$-alkyl, $C_1$–$C_4$-halogenoalkyl, $C_1$–$C_4$-alkoxy, $C_1$–$C_4$-halogenoalkoxy, benzyloxy or silyloxy which is trisubstituted by $C_1$–$C_4$-alkyl and/or phenyl.

$R^3$ and $R^4$ together particularly preferably represent $C_2$–$C_6$-alkylene or the radical (a)

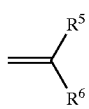

(a)

in which
$R^5$ and $R^6$ independently of one another each represent hydrogen, respectively optionally fluorine-, chlorine- or bromine-substituted $C_1$–$C_4$-alkyl or $C_3$–$C_6$-cycloalkyl, in particular cyclopropyl, cyclopentyl or cyclohexyl, or represent respectively optionally fluorine-, chlorine-, bromine-, hydroxyl, nitro-, $C_1$–$C_4$-alkyl-, $C_1$–$C_4$-halogenoalkyl-, $C_1$–$C_4$-alkoxy-, $C_1$–$C_4$-halogenoalkoxy-, phenoxy-, amino-, $C_1$–$C_4$-alkylamino-, in particular methylamino- or ethylamino- or di-($C_1$–$C_4$)-alkylamino-, in particular dimethylamino- or diethylamino-substituted phenyl, phenyl-$C_1$–$C_4$-alkyl or 5- or 6-membered hetaryl.

$Q^1$ particularly preferably represents oxygen or sulphur.
$Q^2$ particularly preferably represents oxygen.
6,6-Diphenyl-(1,3,4)-oxadiazinane-2,5-dione is excluded from the particularly preferred range.

$R^1$ and $R^2$ independently of one another each very particularly preferably represent hydrogen, $C_1$–$C_{10}$-alkyl, in particular methyl, ethyl, n-propyl, isopropyl, n-butyl, isobutyl, sec-butyl, tert-butyl, n-pentyl, isopentyl, sec-pentyl, tert-pentyl, n-hexyl, isohexyl, sec-hexyl, n-heptyl, isoheptyl, sec-heptyl, oktyl, isooctyl, sec-octyl or 3,7-dimethyloctyl, represent $C_3$–$C_7$-cycloalkyl-$C_1$–$C_4$-alkyl in particular cyclopentylmethyl, cyclohexylmethyl or cycloheptylmethyl, represent respectively optionally fluorine-, chlorine-, bromine-, iodine-, hydroxyl-, cyano-, methyl-, ethyl-, n-propyl-, isopropyl-, n-butyl-, isobutyl-, sec-butyl-, tert-butyl-, trifluoromethyl-, trichloromethyl-, methoxy-, difluoromethoxy-, trifluoromethoxy- or benzyloxy-substituted phenyl, benzyl, phenethyl, 5- or 6-membered hetarylmethyl, in particular thienylmethyl, thiazolylmethyl, furylmethyl or pyridylmethyl or represent indolylmethyl.

$R^1$ and $R^2$ together with the two linking nitrogen atoms very particularly preferably represent a 5- or 6-membered saturated or unsaturated heterocyclic ring, in particular —($CH_2$)$_3$— and —($CH_2$)$_4$—.

$R^3$ and $R^4$ independently of one another each very particularly preferably represent hydrogen, $C_1$–$C_{12}$-alkyl, in particular methyl, ethyl, n-propyl, isopropyl, n-butyl, isobutyl, sec-butyl, tert-butyl, n-pentyl, isopentyl, sec-pentyl, tert-pentyl, n-hexyl, isohexyl, sec-hexyl, n-heptyl, isoheptyl, sec-heptyl, oktyl, isooctyl, sec-octyl, n-decyl or n-dodecyl, represent respectively optionally fluorine- or chlorine-substituted $C_1$–$C_4$-alkyl, in particular fluoromethyl, trifluoromethyl or trichloromethyl, represent $C_2$–$C_6$-alkenyl, in particular vinyl or allyl, represent cyclopentyl or cyclohexyl, represent $C_3$–$C_7$-cycloalkyl-$C_1$–$C_4$-alkyl, in particular cyclopropylmethyl, represent methylthioethyl or represent respectively optionally fluorine-, chlorine-, bromine-, iodine-, hydroxyl-, cyano-, methyl-, ethyl-, n-propyl-, isopropyl-, n-butyl-, isobutyl-, sec-butyl-, tert-butyl-, trifluoromethyl-, trichloromethyl-, methoxy-, difluoromethoxy-, trifluoromethoxy- or benzyloxy-substituted phenyl, phenyl-$C_1$–$C_4$-alkyl, in particular benzyl, 3-naphthylmethyl, benzo-1,3-dioxol-5-yl, thienylmethyl, imidazolylmethyl or indolylmethyl.

$R^3$ and $R^4$ together vere particularly preferably represent —($CH_2$)$_2$—, —$CH(CH_3)CH_2$—, —$C(CH_3)_2CH_2$—, —($CH_2$)$_3$—, —($CH_2$)$_4$—, —($CH_2$)$_5$— or the radical (a)

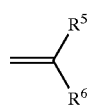

(a)

in which
$R^5$ and $R^6$ independently of one another each represent hydrogen, represent optionally fluorine- or chlorine-substituted methyl, ethyl, n-propyl, isopropyl, n-butyl, isobutyl, sec-butyl or tert-butyl or represent respectively optionally fluorine-, chlorine-, bromine-, nitro-, amino-, methyl-, ethyl-, trifluoromethyl-, methoxy-, difluoromethoxy- or trifluoromethoxy-substituted phenyl, benzyl or pyridyl.

6,6-Diphenyl-(1,3,4)-oxadiazinane-2,5-dione is excluded from the very particularly preferred range.

The general or preferred radical definitions or illustrations listed above can be combined with each other at will, i.e. combinations between the given ranges and preferred ranges are also possible. These radical definitions or illustrations apply both to the end products and, in a corresponding manner, to the starting materials and intermediates.

Preference according to the invention is given to those compounds of the formula (I) which contain a combination of the definitions listed above as being preferred.

Particular preference according to the invention is given to those compounds of the formula (I) which contain a combination of the definitions listed above as being particularly preferred.

Very particular preference according to the invention is given to those compounds of the formula (I) which contain a combination of the definitions listed above as being very particularly preferred.

Saturated or unsaturated hydrocarbon radicals such as alkyl and alkenyl may be, including in combination with hetero atoms such as in alkoxy, for example, straight-chain or branched in each case as far as this is possible.

Optionally substituted radicals may be mono- or polysubstituted, it being possible for the substituents in the case of polysubstitution to be identical or different.

Using, for example, 3-methoxy-2-methyl-2-(tetrahydropyridazine-1-carbothionyloxy)propionic acid as starting material, the course of the reaction in the process (A) according to the invention can be represented by the following equation:

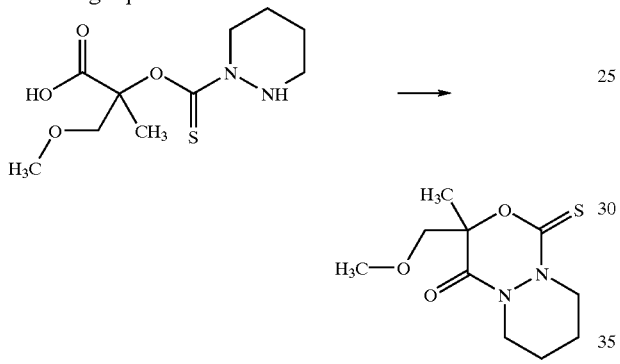

Using, for example, 3-tert-butyl-4-(2-thienylmethyl)-2,5-dioxo-(1,3,4)-oxadiazine and benzyl bromide as starting materials, the course of the reaction in the process (B) according to the invention can be represented by the following equation:

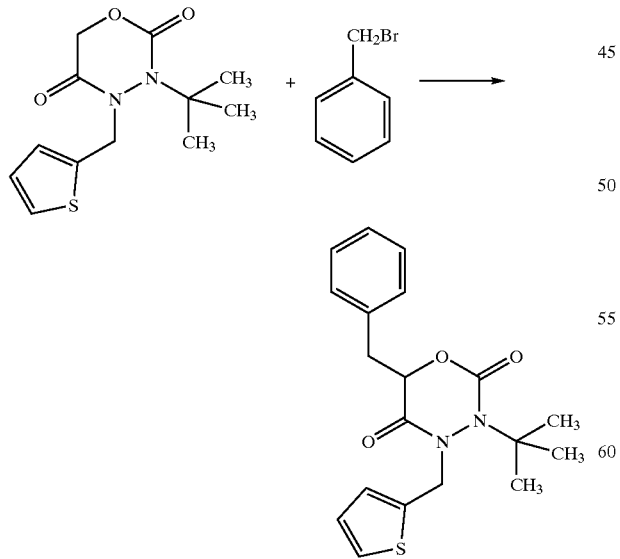

Using, for example, 3,4-dimethyl-2,5-dioxo-(1,3,4)-oxadiazine and acetone as starting materials, the course of the reaction in the process (C) according to the invention can be represented by the following equation:

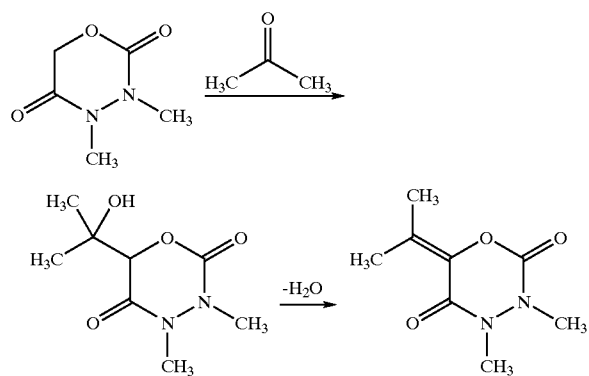

Using, for example, 4,6-dimethyl-6-vinyl-2,5-dioxo-(1,3,4)-oxadiazine and iodomethane as starting materials, the course of the reaction in the process (D) according to the invention can be represented by the following equation:

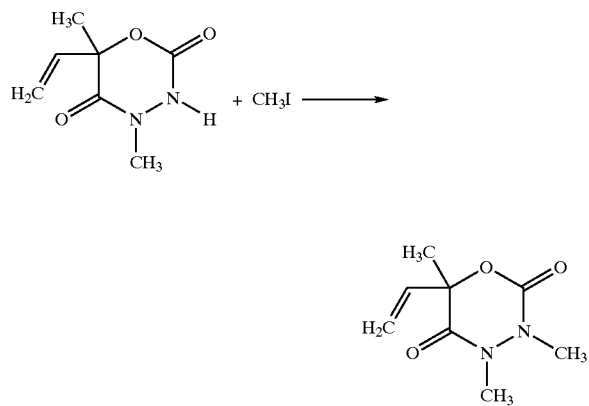

Using, for example, 3-methyl-6-(2-methylpropyl)-2,5-dioxo-(1,3,4)-oxadiazine and dimethyl sulphate as starting materials, the course of the reaction in the process (E) according to the invention can be represented by the following equation:

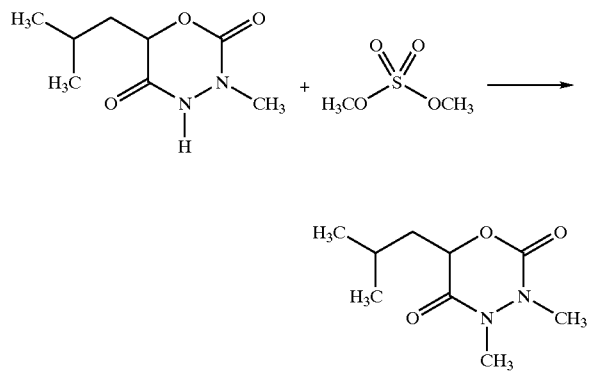

Using, for example, 2'-(4-chlorophenyl)-1'-methyl-(1-hydroxy-2-methyl-cyclopropane)carbohydrazide and phosgene as starting materials, the course of the reaction in the process (F) according to the invention can be represented by the following equation:

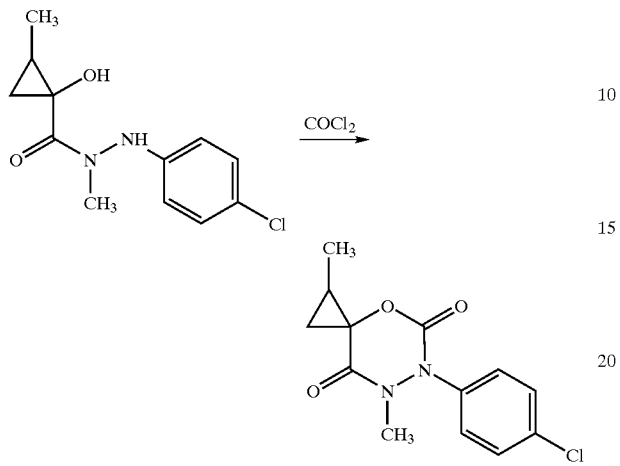

Using, for example, 1'-phenyl-2'-methyl-[3-methyl-2-(4-nitrophenoxycarbonyloxy)]butyrohydrazide as starting

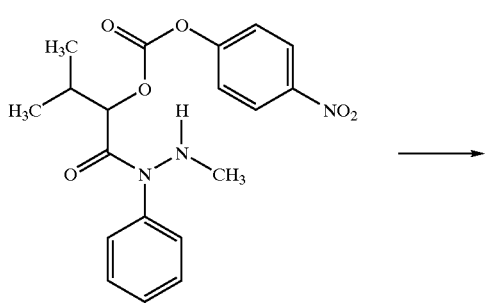

material, the course of the reaction in the process (G) according to the invention can be represented by the following equation:

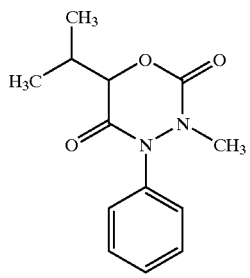

Using, for example, 4-(4-methylpentyl)-3-methyl-6-phenyl-2,5-dioxo-(1,3,4)-oxadiazine and [2,4-bis(4-methoxyphenyl)-1,3,2,4-dithiadiphosphetan-2,4-dithione (Lawesson's reagent) as starting materials, the course of the reaction in the process (H) according to the invention can be represented by the following equation:

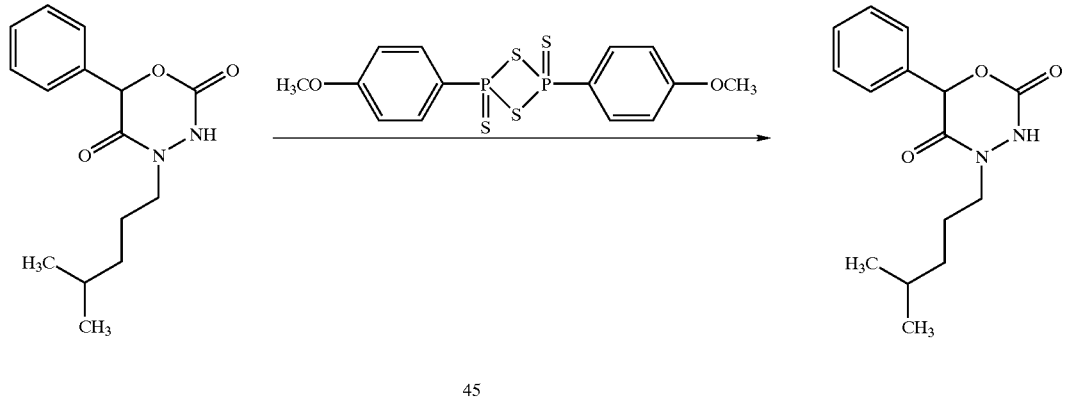

The formula (II) provides a general definition of the carbazates required for carrying out the process (A) according to the invention. In this formula, $R^1$, $R^2$, $R^3$, $R^4$ and $Q^1$ each preferably represent those radicals which have already been mentioned above, in connection with the description of the oxadiazine derivatives of the formula (I), as being preferred substituents. The carbazates of the formula (II) are novel, except for the compounds in which simultaneously $R^2$ and $R^4$ each represent hydrogen, $R^1$ represents $C_1$–$C_5$-alkyl and $R^3$ represents methyl or benzyl (cf. DE-OS (German Published Specification) 2 658 254).

Carbazates of the formula (II) can be prepared, for example, by cleaving off the protective group $A^2$ of C-terminal protected carbazates of the formula (X) in a process (A.a) according to the following equation:

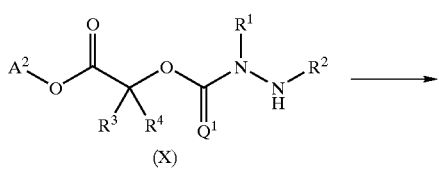

(X)

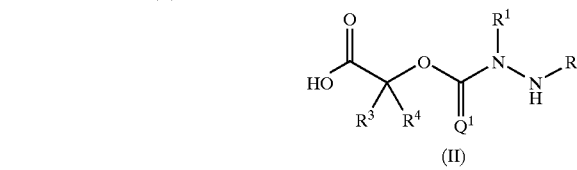

(II)

In the formula (XI), $A^2$ represents a C-terminal protective group such as, for example, tert-butyl or benzyl (cf., for example, T. W. Greene, P. G. M. Wuts, Protective Groups in Organic Synthesis, 2 ed., John Wiley & Sons, New York 1991).

The reaction can be carried out by customary methods for C-terminal deblocking such as acidolysis, for example in the case of a tert-butyl ester, or catalytic hydrogenation, for example in the case of a benzyl ester.

Carbazates of the formula (II) can also be prepared, for example, by cleaving off the 15 protective group $A^3$ of N-terminal protected carbazates of the formula (XI) in a process (A.b) according to the following equation:

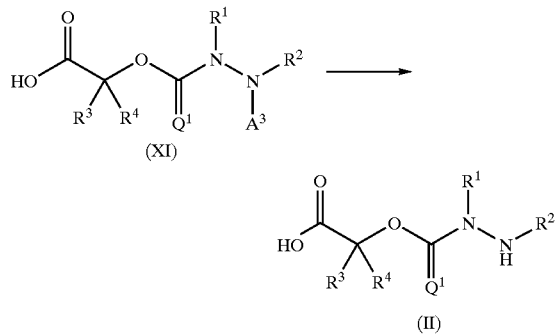

In the formula (X), $A^3$ represents an N-terminal protective group such as, for example, tert-butoxycarbonyl (BOC), benzyloxycarbonyl (Cbz) or benzyl (Bzl) (cf., for example, T. W. Greene, P. G. M. Wuts, Protective Groups in Organic Synthesis, 2 ed., John Wiley & Sons, New York 1991).

The reaction can be carried out by customary methods for N-terminal deblocking such as acidolysis, for example in the case of the BOC group, or catalytic hydrogenation, for example in the case of a benzyl ester.

The C-terminal protected carbazates of the formula (X) required for carrying out the process (A.a) or the N-terminal protected carbazates of the formula (XI) required for carrying the process (A.b) can be prepared starting from N- and C-terminal protected carbazates of the formula (XII)

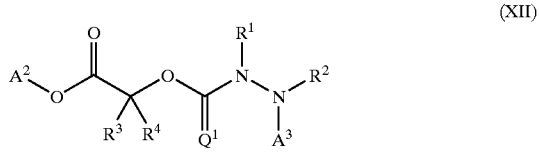

by either cleaving the N-terminal protective group in a process (A.a.b) similar to (A.b) or by cleaving the C-terminal protective group in a process (A.b.a) similar to (A.a). Depending upon the nature of the protective group, it is also possible, in a particular embodiment of the process, to cleave both protective groups in one step and to convert compounds of the formula (XII) directly into compounds of the formula (II) (process A.a/b).

Compounds of the formula (XII) can be prepared, for example, by reacting compounds of the formula (XIII) with carbazates or hydrazines of the formula (XIV), if appropriate in the presence of a diluent, according to the following equation:

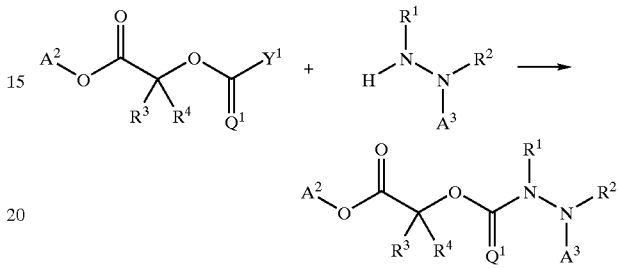

In the formula (XIII), $Y^1$ represents chlorine, trichloromethoxy, $C_1$–$C_4$-alkoxy, optionally substituted phenoxy, 1-imidazolyl or 1,2,4-triazolyl.

Some of the carbazates or hydrazines of the formula (XIV) are known or can be prepared by known methods (cf., for example, J. Chem. Soc. Perkin Trans. I 1975, 1712).

Compounds of the formulae (X) and (XII) are novel, except for the compounds in which $R^2$, $R^4$ each represent hydrogen, $R^1$ represents $C_1$–$C_5$-alkyl and $R^3$ represents methyl or benzyl.

Compounds of the formula (XIII) can be prepared, for example, by reacting protected α-hydroxycarboxylic acids of the formula (XV) with compounds of the formula (VIII) according to the following equation:

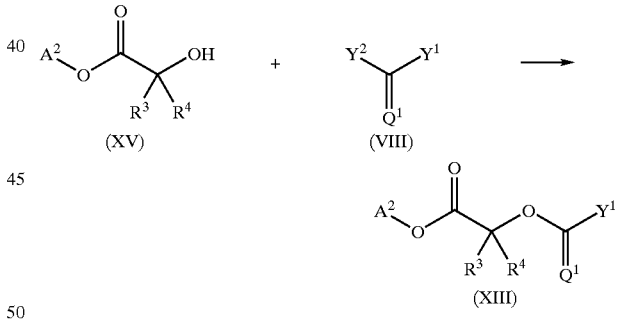

In the formula (VIII), $Y^2$ represents chlorine, trichloromethoxy, 1-imidazolyl or 1,2,4-triazolyl. The compounds of the formula (VIII) are generally known reagents for (thio)phosgenations (cf., for example, Org. Syntheses Coll. Vol. 5, 201 (1973)).

The protected α-hydroxycarboxylic acids of the formula (XV) can be prepared from the free carboxylic acids by generally known methods (for example esterification using alkyl halides or benzyl halides in the presence of caesium carbonate, J. Chem. Soc. Perkin Trans. I 1993, 11). α-Hydroxycarboxylic acids are commercially available or can be prepared, for example, from α-amino acids via deamination (cf., for example, Tetrahedron Letters 28, 1873 (1987) and 26, 5257 (1985); Compr. Org. Chem. Vol. 2, 739–778 (1979); Ullmanns Encyclopädie Techn. Chem. 4th ed. (1977), Volume 13, 163).

Compounds of the formula (XII) in which $Q^1$ represents oxygen (XII-1) can also be prepared, for example, by reacting compounds of the formula (XVI) with the formula (XVII), if appropriate in the presence of a diluent, according to the following equation:

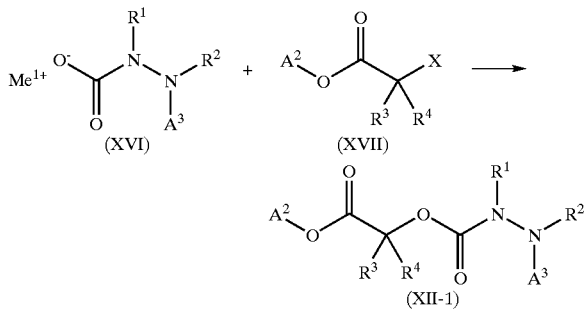

In the formula (XVI), $Me^1$ represents an alkali metal, preferably potassium or caesium. In the formula (XVII), X represents chlorine, bromine, alkanesulphonyl, in particular methanesulphonyl or trifluoromethanesulphonyl or arenesulphonyl, in particular benzenesulphonyl or p-toluenesulphonyl.

Compounds of the formula (XVI) can be prepared by reacting the carbazates or hydrazines of the formula (XIV) described further above with alkali metal carbonates, preferably potassium carbonate or caesium carbonate, if appropriate in the presence of carbon dioxide.

Compounds of the formula (XVII) can be prepared, for example, by generally known methods from the abovementioned derivatives of α-hydroxycarboxylic acids. Furthermore, compounds of the formula (XVII) in which X represents bromine or chlorine can be prepared, for example, by initially converting α-amino acids into α-chloro- or bromo-carboxylic acids (cf. J. Am. Chem. Soc. 76, 6054 (1954); Advances in Protein Chemistry Vol. IV, M. L. Anson, J. T. Edsall (Eds.) 1948, 33) and protecting these by generally known methods.

The oxadiazines of the formula (I-c) required for carrying out the processes (B) and (C) according to the invention constitute a sub-group of the compounds of the general formula (I) according to the invention and can be prepared, for example, by processes (A) and (D) to (H).

The formula (III) provides a general definition of the compounds furthermore required for carrying out the process (B). In this formula, $R^{4-1}$ preferably represents the radicals which have already been mentioned, in connection with the description of the oxadiazine derivatives of the formula (I), as being preferred for $R^4$, with the exception of hydrogen. E preferably represents halogen, in particular chlorine or bromine, in the case where $R^{4-1}$ represents one of the optionally substituted alkyl radicals, also mesyloxy, tosyloxy or trifluoromethylsulphonyloxy or, in the case that $R^{4-1}$ represents a carbonyl radical, the grouping —$OR^{4-1}$.

The alkylating or acylating reagents of the formula (III) are generally known reagents of organic chemistry and/or can be prepared by known methods.

The formula (IV) provides a general definition of the aldehydes or ketones required for carrying out the process (C) according to the invention. In this formula, $R^5$ and $R^6$ each preferably represent those radicals which have already been mentioned in connection with the description of the oxadiazine derivatives of the formula (I) as being preferred substituents.

Aldehydes and ketones of the formula (IV) are generally known and/or can be prepared by known methods.

The oxadiazines of the formula (I-e) and (I-f) required for carrying out the processes (D) and (E) according to the invention, respectively, constitute sub-groups of the compounds of the formula (I) according to the invention and can be prepared, for example, by processes (A) to (C) and (F) to (H).

The formulae (V) and (VI) provide a general definition of the compounds furthermore required for carrying out the processes (D) and (E). In these formulae, $R^{1-1}$ and $R^{2-1}$ preferably represent those radicals which have already been mentioned as being preferred for $R^1$ and $R^2$, respectively, in connection with the description of the oxadiazine derivatives of the formula (I), except for hydrogen, and E correspondingly preferably represents the radicals mentioned in the description of the compounds of the formula (III). Correspondingly means that for carboxylic anhydrides of the formulae (V) and (VI) the groupings —$OR^{1-1}$ and —$OR^{2-1}$, respectively, may replace —$OR^{4-1}$.

The alkylating or acylating reagents of the formulae (V) and (VI) are generally known reagents of organic chemistry and/or can be prepared by known methods.

The formula (VII) provides a general definition of the compounds required for carrying out the process (F) according to the invention. In this formula, $R^1$, $R^2$, $R^3$, $R^4$ and $Q^2$ each preferably represent those radicals which have already been mentioned in connection with the description of the oxadiazine derivatives of the formula (I) as being preferred substituents.

Compounds of the formula (VII) can be prepared, for example, by cleaving the N-terminal protective group $A^3$ of compounds of the formula (XVIII) by customary methods, mentioned further above, according to the following equation:

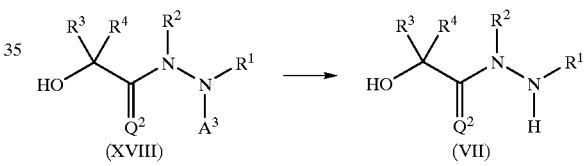

α-Hydroxy(thio)carbohydrazides of the formula (XVIII) can be prepared, for example, by reacting α-hydroxy(thio) carboxylic esters of the formula (XIX) with hydrazines of the formula (XX) according to the following equation:

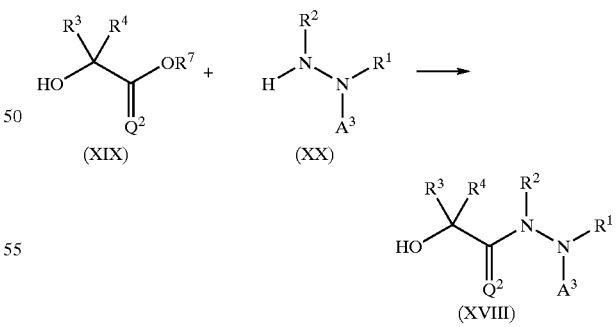

In the formula (XIX), $R^7$ represents optionally substituted alkyl or aryl. The α-hydroxy(thio)carboxylates of the formula (XIX) are commercially available or can be prepared, for example, from a-amino acids via deamination (cf., for example, Tetrahedron Letters 28, 1873 (1987) and 26, 5257 (1985); Compr. Org. Chem. Vol. 2, 739–778 (1979); Ullmanns Encyclopädie Techn. Chem. 4th edition (1977), Volume 13, 163).

Some hydrazines of the formula (XX) are known, or they can be obtained by known methods (cf., for example, J. Chem. Soc. Perkin Trans. I 1975, 1712).

The formula (IX) provides a general definition of the compounds required for carrying out the process (G) according to the invention. In this formula, $R^1$, $R^2$, $R^3$, $R^4$, $Q^1$ and $Q^2$ each preferably represent those radicals which have already been mentioned in connection with the description of the oxadiazine derivatives of the formula (I) as being preferred substituents. $Y^1$ preferably represents chlorine, trichloromethoxy, 1-imidazolyl, 1,2,4-triazolyl or Z-substituted aryloxy, in particular pentafluorophenyl, 4-nitrophenyl or 2,4-dinitrophenyl.

Compounds of the formula (IX) can be prepared, for example, by cleaving the N-terminal protective group $A^3$ of compounds of the formula (XXI) by methods mentioned further above according to the following equation:

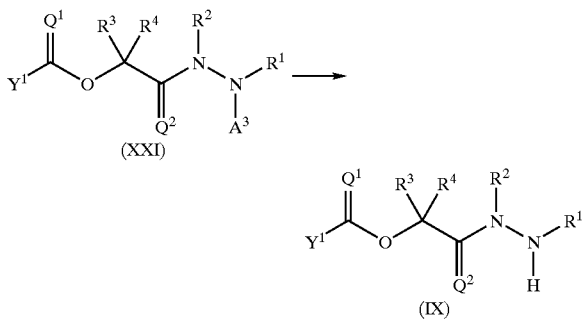

Compounds of the formula (XXI) can be prepared, for example, by reacting α-hydroxy(thio)carbohydrazides of the formula (XVIII) described above with (thio)phosgenating reagents of the formula (VIII) described further above and, if appropriate, reacting the resulting product of the formula (XXI) in which $Y^1$ does not yet represent Z-substituted aryloxy with an appropriate phenol or phenolate such as, for example, 2,4-dinitrophenol.

The oxadiazines of the formula (I-a) required for carrying out the process (H) according to the invention constitute sub-groups of the compounds of the general formula (I) according to the invention and can be prepared, for example, by processes (A) to (G).

The preferred thionylating reagents furthermore required for carrying out the process (H) according to the invention are phosphorus pentasulphide or 2,4-bis(4-methoxyphenyl)-1,3,2,4-dithiadiphosphetan-2,4-dithione (Lawesson's reagent).

Suitable reaction auxiliaries for carrying out the process (A) according to the invention are all compounds which are suitable for forming an amide bond (cf., for example, Houben-Weyl, Methoden der Organischen Chemie, Volume 15/2; Bodensky et al.; Peptide Synthesis 2nd ed., Wiley & Sons, New York 1976). The following methods are preferred: activated ester method using pentafluorophenol (PfP), N-hydroxysuccinimide, 1-hydroxybenzotriazole, coupling with carbodiimides such as dicyclohexylcarbodiimide or N'-(3-dimethylaminopropyl)-N-ethylcarbodiimide (EBC) and the mixed-anhydride-method or coupling with phosphonium reagents such as 1-benzotriazolyloxy-tris-(dimethylaminophosphonium) hexafluorophosphate (BOP), bis-(2-oxo-3-oxazolidinyl)phosphoryl chloride (BOP-Cl) or using phosphonic ester reagents such as diethyl cyanophosphonate (DEPC) and diphenylphosphoryl azide (DPPA). Particular preference is given to the coupling with bis-(2-oxo-3-oxazolidinyl)-phosphoryl chloride (BOP-Cl) and N'-(3-dimethylaminopropyl)-N-ethylcarbodiimide (EDC) in the presence of 1-hydroxybenzotriazole (HOBt).

Suitable diluents for carrying out the process (A) according to the invention are organic solvents and any mixtures thereof. Examples include: aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, methylene chloride, chloroform, carbon tetrachloride, dichloro-, trichloroethane or tetrachloroethylene; ethers, such as diethyl, diisopropyl, methyl t-butyl, methyl t-amyl ether, dioxane, tetrahydrofuran, 1,2-dimethoxyethane, 1,2-diethoxyethane, diethylene glycol dimethyl ether or anisole; ketones, such as acetone, butanone, methyl isobutyl ketone or cyclohexanone; nitriles, such as acetonitrile, propionitrile, n- or i-butyronitrile or benzonitrile; amides, such as formamide, N,N-dimethylfornamide, N,N-dimethylacetamide, N-methylformanilide, N-methylpyrrolidone, 1,3-dimethyltetrahydro-2-pyrimidinone (DMPU), 1,3-dimethyl-2-imidazolidinone, tetramethylurea or hexamethylphosphoric triamide; N-oxides, such as N-methylmorpholine N-oxide; esters, such as methyl, ethyl or butyl acetate; sulphoxides, such as dimethyl sulphoxide; sulphones, such as sulpholane.

The cyclization is preferably carried out in the presence of a base. Suitable bases are inorganic or organic bases. These preferably include alkaline earth metal or alkali metal hydroxides, alkoxides, acetates, carbonates or bicarbonates, such as, for example, sodium hydroxide, potassium hydroxide or ammonium hydroxide, sodium methoxide, sodium ethoxide, potassium tert-butoxide, sodium acetate, potassium acetate, calcium acetate or ammonium acetate, sodium carbonate, potassium carbonate or ammonium carbonate, sodium bicarbonate or potassium bicarbonate and also tertiary amines, such as trimethylamine, triethylamine, tributylamine, ethyl-diisopropylamine, N,N-dimethylaniline, N,N-dimethyl-benzylamine, pyridine, picoline, N-methylpiperidine, N-methylmorpholine, N,N-dimethylaminopyridine, diazabicyclooctane (DABCO), diazabicyclononene (DBN) or diazabicycloundecene (DBU).

The reaction temperature in the process (A) according to the invention can be varied within a relatively wide range. The cyclization is generally carried out at temperatures between −40° C. and +150° C., preferably at −20° C. to 100° C., particularly preferably at 0° C. to room temperature.

When carrying out the process (A) according to the invention, the compound of the formula (II) and the base are generally employed in a molar ratio of 1:1 to 1:3, preferably 1:2.

The process (B) according to the invention can be carried out in the presence of a diluent. Suitable diluents are water, organic solvents and any mixtures thereof. Examples include: aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, methylene chloride, chloroform, carbon tetrachloride, dichloro-, trichloroethane or tetrachloroethylene; ethers, such as diethyl, diisopropyl, methyl t-butyl, methyl t-amyl ether, dioxane, tetrahydrofuran, 1,2-dimethoxyethane, 1,2-diethoxyethane, diethylene glycol dimethyl ether or anisole; amides, such as formamide, N,N-dimethylformamide, N,N-dimethylacetamide, N-methylformanilide, N-methylpyrrolidone or hexamethylphosphoric triamide;

N-oxides, such as N-methylmorpholine N-oxide; esters, such as methyl, ethyl or butyl acetate; sulphoxides, such as dimethyl sulphoxide; sulphones, such as sulpholane; alcohols, such as methanol, ethanol, n- or i-propanol, n-, iso-, sec- or tert-butanol, ethanediol, propane-1,2-diol, ethoxyethanol, methoxyethanol, diethylene glycol monomethyl ether or diethylene glycol monoethyl ether; water.

The process (B) according to the invention is preferably carried out in the presence of a suitable reaction auxiliary. Suitable reaction auxiliaries are all customary inorganic or organic bases. These preferably include alkaline earth metal or alkali metal hydrides, hydroxides, alkoxides, amides, acetates, carbonates or bicarbonates, such as, for example, sodium hydride, sodium hydroxide, potassium hydroxide or ammonium hydroxide, sodium methoxide, sodium ethoxide, potassium tert-butoxide, sodium amide, lithium diisopropylamide, lithium bis(trimethylsilyl) amide, sodium bis(trimethylsilyl) amide, potassium bis(trimethylsilyl) amide, sodium acetate, potassium acetate, calcium acetate or ammonium acetate, sodium carbonate, potassium carbonate or ammonium carbonate, sodium bicarbonate or potassium bicarbonate; lithium alkyls such as methyl-, n-butyl-, sec-butyl- or tert-butyllithium and also tertiary amines, such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU).

The reaction temperature in the process (B) according to the invention can be varied within a relatively wide range. In general, the reaction is carried out at temperatures between –100° C. and +150° C., preferably between –78° C. and 100° C.

When carrying out the process (B) according to the invention, the oxadiazine derivative of the formula (I-c), the reagent of the formula (III) and the base are generally employed in each case in approximately equimolar amounts. However, it is also possible to employ a relatively large excess (up to 50 mol) of reagent and base.

The process (C) according to the invention can be carried out in the presence of a diluent. Suitable diluents are preferably those listed for process (B).

The process (C) according to the invention is preferably carried out in the presence of a suitable reaction auxiliary. Suitable reaction auxiliaries are preferably all bases listed for process (B).

The reaction temperature in the process (C) according to the invention can be varied within a relatively wide range. In general, the reaction is carried out at temperatures between –100° C. and +120° C., preferably between –78° C. and 100° C.

To eliminate water, if this does not take place without assistance, an acid may be used. Suitable acids are all inorganic and organic protic and also Lewis acids, and also all polymeric acids. These include, for example, hydrogen chloride, sulphuric acid, phosphoric acid, formic acid, acetic acid, trifluoroacetic acid, methanesulphonic acid, trifluoromethanesulphonic acid, toluenesulphonic acid, boron trifluoride (also as etherate), boron tribromide, aluminium trichloride, zinc chloride, iron(III) chloride, antimony pentachloride, acidic ion exchangers, acidic aluminas and acidic silica gel.

When carrying out process (C) according to the invention, the oxadiazine derivative of the formula (I-c), the carbonyl compound of the formula (IV) and the base are generally in each case employed in approximately equimolar amounts. However, it is also possible to employ a relatively large excess (up to 50 mol) of reagent and base.

The processes (D) and (E) according to the invention can be carried out in the presence of a diluent. Preferred diluents are the diluents listed for process (B).

The processes (D) and (E) according to the invention are preferably carried out in the presence of a suitable reaction auxiliary. Suitable reaction auxiliaries are all bases listed for process (B). Additionally, they also include catalysts such as, for example, 4-(N,N-dimethylamino)-pyridine.

The reaction temperatures in the processes (D) and (E) according to the invention can be varied within a relatively wide range. In general, the reaction is carried out at temperatures between –40° C. and +120° C., preferably between –10° C. and 100° C.

When carrying out the processes (D) and (E) according to the invention, the oxadiazine derivative of the formula (I-g) or (I-h), the compound of the formula (V) or (VI) and the base are generally in each case employed in approximately equimolar amounts. However, it is also possible to employ a relatively large excess (up to 50 mol) of reagent and base. If appropriate, amounts of catalyst of 0.001 to 0.1 mole per mol of oxadiazine derivative are employed.

The process (F) according to the invention can be carried out in the presence of a diluent. Preferred diluents are the diluents listed for process (A).

The process (F) according to the invention can be carried out in the presence of a suitable reaction auxiliary. Suitable reaction auxiliaries are all bases listed for process (A).

The reaction temperature in the process (F) according to the invention can be varied within a relatively wide range. In general, the reaction is carried out at temperatures between –20° C. and +150° C., preferably between +20° C. and 120° C., the cyclization optionally being initiated by an increase in temperature after the reaction of the two reactants.

When carrying out the process (F) according to the invention, 1.0 to 2.0 mol, preferably 1.0 to 1.2 mol of the compound (VIII) and optionally 1.0 to 5 mol of reaction auxiliary are employed per mole of the compound of the formula (VII).

The process (G) according to the invention can be carried out in the presence of a diluent. Preferred diluents are the diluents listed in process (A).

The process (G) according to the invention can be carried out in the presence of a suitable reaction auxiliary. Suitable reaction auxiliaries are all bases listed in process (A).

The reaction temperature in the process (G) according to the invention can be varied within a relatively wide range. In general, the reaction is carried out at temperatures between –20° C. and +150° C., preferably between +20° C. and 120° C.

When carrying out the process (G) according to the invention, the compound of the formula (II) and the base are generally employed in a molar ratio of 1:1 to 1:3, preferably in equimolar amounts.

The process (H) according to the invention can be carried out in the presence of a diluent. Suitable diluents are organic solvents and any mixtur es thereof. Examples include: aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, methylene chloride, chloroform, carbon tetrachloride, dichloro-, trichloroethane or tetrachloroethylene; ethers, such as diethyl, diisopropyl, methyl t-butyl, methyl t-amyl ether, dioxane, tetrahydrofuran, 1,2-dimethoxyethane, 1,2-diethoxyethane, diethylene glycol dimethyl ether or anisole; ureas, such as 1,3-dimethyl-tetrahydro-2-pyrimidinone (DMPU), 1,3-dimethyl-2-imidazolidinone, tetramethylurea; hexamethylphosphoric triamide; sulphoxides, such as dimethyl sulphoxide; sulphones, such as sulpholane.

The reaction temperature in the process (H) according to the invention can be varied within a relatively wide range. In general, the reaction is carried out at temperatures between 0° C. and +150° C., preferably between +20° C. and 100° C.

When carrying out the process (H) according to the invention, in general 1 to 20, preferably 1 to 5 mol of sulphurizing reagent are employed per mole of the compound of the formula (I-a).

The reactions of the processes according to the invention can be carried out at atmospheric pressure or under elevated pressure and are preferably carried out at atmospheric pressure. Work-up is carried out by customary methods of organic chemistry. The end products are preferably purified by crystallization, chromatographic purification or by removing the volatile components, if appropriate under reduced pressure.

The active compounds are suitable for controlling pathogenic endoparasites encountered in humans and in animal husbandry and livestock breeding, in productive livestock, breeding stock, zoo animals, laboratory animals, animals used in experiments, and pets, and have low toxicity towards warm-blooded animals. They are active against resistant and normally sensitive species and against all or some stages of development of the pests. By controlling the pathogenic endoparasites, it is intended to reduce disease, mortality and decreasing performance (for example in the production of meat, milk, wool, hides, eggs, honey, etc.), so that more economical and simpler animal keeping is possible by using the active compounds. The pathogenic endoparasites include cestodes, trematodes, nematodes, in particular:

From the order of the Pseudophyllidea, for example Diphyllobothrium spp., Spirometra spp., Schistocephalus spp., Ligula spp., Bothridium spp., Diphlogonoorus spp.

From the order of the Cyclophyllidea, for example Mesocestoides spp., Anoplocephala spp., Paranoplocephala spp., Moniezia spp., Thysanosmsa spp., Thysaniezia spp., Avitellina spp., Stilesia spp., Cittotaenia spp., Anhyra spp., Bertiella spp., Taenia spp., Echinococcus spp., Hydratigera spp., Davainea spp., Raillietina spp., Hymenolepsis spp., Echinolepsis spp., Echinocotyle spp., Diorchis spp., Dipylidium spp., Joyeuxiella spp., Diplopylidium spp.

From the subclass of the Monogenea, for example Cyrodactylus spp., Dactylogyrus spp., Polystoma spp.

From the subclass of the Digenea, for example Diplostomum spp., Posthodiplostomum spp., Schistosoma spp., Trichobilharzia spp., Omithobilharzia spp., Austrobilharzia spp., Gigantobilharzia spp., Leucochloridium spp., Brachylaima spp., Echinostoma spp., Echinoparyphium spp., Echinochasmus spp., Hypoderaeum spp., Fasciola spp., Fasciolides spp., Fasciolopsis spp., Cyclocoelum spp., Typhloccelum spp., Paramphistomum spp., Calicophoron spp, Cotylophoron spp., Gigantocotyle spp., Fischoederius spp., Gastrothylacus spp., Notocotylus spp., Catatropis spp., Plagiorchis spp., Prosthogonismus spp., Dicrocoelium spp., Collyriclum spp., Nanophyetus spp., Opisthorchis spp., Clonorchis spp., Metorchis spp., Heterophyes spp., Metagonimus spp.

From the order of the Enoplida, for example Trichuris spp., Capillaria spp., Trichlom-osoides spp., Trichinella spp.

From the order of the Rhabditia, for example Micronema spp., Strongyloides spp.

From the order of the Strongylida, for example Stronylus spp., Triodontophorus spp., Oesophagodontus spp., Trichonema spp., Gyalocephalus spp., Cylindropharynx spp., Poteriostomum spp., Cyclococercus spp., Cylicostephanus spp., Oesophagostomum spp., Chabertia spp., Stephanurus spp., Acylostoma spp., Uncinaria spp., Bunostomum spp., Globocephalus spp., Syngamus spp., Cyathostoma spp., Metastrongylus spp., Dictyocaulus spp., Muellerius spp., Protostrongylus spp., Neostrongylus spp., Cystocaulus spp., Pneumostrongylus spp., Spicocaulus spp., Elaphostrongylus spp., Parelaphostrongylus spp., Crenosoma spp., Paracrenosoma spp., Angiostrongylus spp., Aelurostrongylus spp., Filaroides spp., Parafilaroides spp., Trichostrongylus spp., Haemonchus spp., Ostertagia spp., Marshallagia spp., Cooperia spp., Nematodirus spp., Hyostrongylus spp., Obeliscoides spp., Amidostomum spp., Ollulanus spp.

From the order of the Oxyurida, for example Oxyuris spp., Enterobius spp., Passalurus spp., Syphacia spp., Aspiculuris spp., Heterakis spp.

From the order of the Ascaridia, for example Ascaris spp., Toxascaris spp., Toxocara spp., Parascaris spp., Anisakis spp., Ascaridia spp.

From the order of the Spirurida, for example Gnathostoma spp., Physaloptera spp., Thelazia spp., Gongylonema spp., Habronema spp., Parabronema spp., Draschia spp., Dracunculus spp.

From the order of the Filariida, for example Stephanofilaria spp., Parafilaria spp., Setaria spp., Loa spp., Dirofilaria spp., Litomosoides spp., Brugia spp., Wuchereria spp., Onchocerca spp.

From the group of the Gigantohynchida, for example Filicollis spp., Moniliformis spp., Macracanthorhynchus spp., Prosthenorchis spp.

For example, they have outstanding activity against nematodes such as *Haemonchus contortus*.

The livestock and breeding stock include mammals, such as, for example, cattle, horses, sheep, pigs, goats, camels, water buffalo, donkeys, rabbits, fallow deer, reindeer, fur-bearing animals, such as, for example, minks, chinchilla or racoons, birds, such as, for example, chickens, geese, turkeys or ducks, freshwater fish and sea fish, such as, for example, trout, carp and eels, reptiles and insects, such as, for example, honey bee and silkworm.

The laboratory and test animals include mice, rats, guinea pigs, golden hamsters, dogs and cats.

The pets include dogs and cats.

Administration can be effected prophylactically as well as therapeutically.

The active substances are administered, either directly or in the form of suitable preparations, enterally, parenterally, dermally, nasally, by treating the habitat or with the aid of shaped articles containing the active compound, such as, for example, strips, plates, tapes, collars, ear tags, limb bands or marking devices.

Enteral administration of the active compounds is effected for example orally in the form of powders, suppositories, tablets, capsules, pastes, drinks, granules, solutions, suspensions and emulsions which can be applied orally, boluses, medicated feed or drinking water. Dermal application is effected, for example, in the form of dipping, spraying, bathing, washing, or pouring-on and spotting-on, and powdering. Parenteral administration is effected, for example, in the form of injection (intramuscular, subcutaneous, intravenous or intraperitoneal) or by implants.

Suitable preparations include:

Solutions, such as solutions for injection, oral solutions, concentrates for oral administration after dilution, solutions for use on the skin or in body cavities, pour-on formulations, gels;

Emulsions and suspensions for oral or dermal administration and for injection; semi-solid preparations;

Formulations in which the active compound is incorporated in a cream base or in an oil-in-water or water-in-oil emulsion base;

Solid preparations, such as powders, premixes or concentrates, granules, pellets, tablets, boluses, capsules; aerosols and inhalants, shaped articles containing the active compound.

Solutions for injection are administered intravenously, intramuscularly and subcutaneously.

Solutions for injection are prepared by dissolving the active compound in a suitable solvent and, if desired, adding additives, such as solubilizers, acids, bases, buffer salts, antioxidants, or preservatives. The solutions are sterile-filtered and decanted into containers.

Suitable solvents include: physiologically acceptable solvents, such as water, alcohols, such as ethanol, butanol, benzyl alcohol, glycerol, hydrocarbons, propylene glycol, polyethylene glycols and N-methylpyrrolidone, and their mixtures.

If appropriate, the active compounds can also be dissolved in physiologically acceptable vegetable or synthetic oils which are suitable for injection.

Suitable solubilizers include: solvents which facilitate the dissolution of the active compound in the main solvent or which prevent precipitation of the active compound. Examples of solubilizers are polyvinylpyrrolidone, polyethoxylated castor oil and polyethoxylated sorbitan esters.

The following are preservatives: benzyl alcohol, trichlorobutanol, p-hydroxybenzoic esters or n-butanol.

Oral solutions are administered directly. Concentrates are first diluted to the administration concentration and then administered orally. Oral solutions and concentrates are prepared as described above in the case of the solutions for injection, sterile procedures not being necessary.

Solutions for use on the skin are applied drop by drop, smoothed on, rubbed in, splashed on or sprayed on, or applied by dipping, bathing or washing. These solutions are prepared as described above in the case of the solutions for injection.

It may be advantageous to add thickeners in the preparation process. The following are thickeners: inorganic thickeners, such as bentonites, colloidal silica, aluminium monostearate, or organic thickeners, such as cellulose derivatives, polyvinyl alcohols and their copolymers, acrylates and methacrylates.

Gels are applied to the skin or smoothed on or introduced into body cavities. Gels are prepared by adding such an amount of thickener to solutions which have been prepared as described for the solutions for injection that a clear composition is formed which has an ointment-like consistency. The thickeners used are the thickeners indicated further above.

Pour-on and spot-on formulations are poured or splashed onto limited areas of the skin, the active compound penetrating the skin and acting systemically, or spreading on the body surface.

Pour-on and spot-on formulations are prepared by dissolving, suspending or emulsifying the active compound in suitable solvents or solvent mixtures which are tolerated by the skin. If appropriate, other auxiliaries, such as colorants, absorption promoters, antioxidants, photostabilizers or tackifiers are added.

Suitable solvents include: water, alkanols, glycols, polyethylene glycols, polypropylene glycols, glycerol, aromatic alcohols, such as benzyl alcohol, phenylethanol or phenoxyethanol, esters, such as ethyl acetate, butyl acetate or benzyl benzoate, ethers, such as alkylene glycol alkyl ethers, such as dipropylene glycol monomethyl ether or diethylene glycol mono-butyl ether, ketones, such as acetone or methyl ethyl ketone, aromatic and/or aliphatic hydrocarbons, vegetable or synthetic oils, DMF, dimethylacetamide, N-methylpyrrolidone, 2,2-dimethyl-4-oxymethylene-1,3-dioxolane.

Colorants are all colorants which can be dissolved or suspended and which are approved for use in animals.

Examples of absorption promoters are DMSO, spreading oils, such as isopropyl myristate, dipropylene glycol pelargonate, silicone oils, fatty acid esters, triglycerides or fatty alcohols.

The following are antioxidants: sulphites or metabisulphites, such as potassium metabisulphate, ascorbic acid, butylhydroxytoluene, butylhydroxyanisole or tocopherol.

Example of photostabilizers are compounds from the class of the benzophenones or novantisolic acid.

Tackifiers are, for example, cellulose derivatives, starch derivatives, polyacrylates or natural polymers such as alginates or gelatin.

Emulsions can be administered orally, dermally or as injections.

Emulsions are either the water-in-oil type or the oil-in-water type.

They are prepared by dissolving the active compound either in the hydrophobic or in the hydrophilic phase and by homogenizing this phase with the solvent of the other phase, with the aid of suitable emulsifiers and, if appropriate, other auxiliaries, such as colorants, absorption promoters, preservatives, antioxidants, photostabilizers, and viscosity-increasing substances.

Suitable hydrophobic phases (oils) include: paraffin oils, silicone oils, natural vegetable oils such as sesame seed oil, almond oil or castor oil, synthetic triglycerides, such as caprylic/capric acid biglyceride, a triglyceride mixture with vegetable fatty acids of chain length $C_{8-12}$ or other specifically selected natural fatty acids, mixtures of partial glycerides of saturated or unsaturated fatty acids which may also contain hydroxyl groups, and mono- and diglycerides of the $C_8/C_{10}$-fatty acids.

Fatty acid esters, such as ethyl stearate, di-n-butyryl adipate, hexyl laurate, dipropylene glycol pelargonate, esters of a branched fatty acid having a medium chain length with saturated fatty alcohols of chain length $C_{16}$–$C_{18}$, isopropyl myristate, isopropyl palmitate, caprylic/capric esters of saturated fatty alcohols of chain length $C_{12}$–$C_{18}$, isopropyl stearate, oleyl oleate, decyl oleate, ethyl oleate, ethyl lactate, waxy fatty acid esters such as artificial duck uropygial fat, dibutyl phthalate, diisopropyl adipate, ester mixtures related to the latter, etc.

Fatty alcohols, such as isotridecyl alcohol, 2-octyldodecanol, cetylstearyl alcohol or oleyl alcohol.

Fatty acids, such as, for example, oleic acid and its mixtures.

Suitable hydrophilic phases include:
water, alcohols, such as, for example, propylene glycol, glycerol, sorbitol and their mixtures.

Suitable emulsifiers include: nonionic surfactants, for example polyethoxylated castor oil, polyethoxylated sorbitan monooleate, sorbitan monostearate, glycerol monostearate, polyoxyethyl stearate or alkylphenol polyglycol ethers;

ampholytic surfactants, such as disodium N-lauryl-β-iminodipropionate or lecithin;

anionic surfactants, such as Na lauryl sulfate, fatty alcohol ether sulfates, and the monoethanolamine salt of mono/dialkylpolyglycol ether orthophosphoric ester;

cationic surfactants, such as cetyltrimethylammonium chloride.

Suitable other auxiliaries include: substances which increase the viscosity and stabilize the emulsion, such as carboxymethylcellulose, methylcellulose and other cellulose and starch derivatives, polyacrylates, alginates, gelatin, gum arabic, polyvinylpyrrolidone, polyvinyl alcohol, methylvinyl ether/maleic anhydride copolymers, polyethylene glycols, waxes, colloidal silica, or mixtures of the listed substances.

Suspensions can be administered orally, dermally or as an injection. They are prepared by suspending the active compound in a liquid excipient, if appropriate with the addition of other auxiliaries, such as wetting agents, colorants, absorption promoters, preservatives, antioxidants and photostabilizers.

Suitable liquid excipients include all homogeneous solvents and solvent mixtures.

Suitable wetting agents (dispersants) include the surfactants indicated further above.

Suitable other auxiliaries include those indicated further above.

Semi-solid preparations can be administered orally or dermally. They are only distinguished from the above-described suspensions and emulsions by their higher viscosity.

To prepare solid preparations, the active compound is mixed with suitable excipients, if appropriate with the addition of auxiliaries, and the mixture is formulated as desired.

Suitable excipients include all physiologically acceptable solid inert substances. Suitable for this purpose are inorganic and organic substances. Inorganic substances are, for example, common salt, carbonates, such as calcium carbonate, hydrogen carbonates, aluminium oxides, silicas, clays, precipitated or colloidal silica, and phosphates.

Organic substances are, for example, sugars, cellulose, foodstuffs and animal feeds, such as powdered milk, animal meals, cereal meals, coarse cereal meals and starches.

Auxiliaries are preservatives, antioxidants and colorants which have already been mentioned further above.

Other suitable auxiliaries are lubricants and glidants, such as, for example, magnesium stearate, stearic acid, talc, bentonites, disintegrants, such as starch or crosslinked polyvinylpyrrolidone, binders, such as, for example, starch, gelatin or linear polyvinylpyrrolidone, and dry binders, such as microcrystalline cellulose.

In the preparations, the active compounds can also be present in mixtures with synergists or other active compounds which are active against pathogenic endoparasites. Examples of such active compounds are L-2,3,5,6-tetrahydro-6-phenyl-imidazolylthiazole, benzimidazole carbamates, praziquantel, pyrantel or febantel.

Ready-to-use preparations contain the active compound in concentrations of 10 ppm to 20 percent by weight, preferably from 0.1 to 10 percent by weight.

Preparations which are diluted before use contain the active compound in concentrations of 0.5 to 90 percent by weight, preferably from 5 to 50 percent by weight.

In general, it has proven advantageous to administer amounts of about 1 to 100 mg of active compound per kg of body weight per day to obtain effective results.

The active compounds are furthermore suitable for controlling animal pests, in particular insects, arachnids and nematodes, encountered in agriculture, in forestry, in the protection of stored products and of materials, and in the hygiene field, and have good plant tolerance and low toxicity to warm-blooded animals. They are active against normally sensitive and resistant species and against all or some stages of development.

The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Pediculus humanus corporis,* Haematopinus spp. and Linognathus spp.

From the order of the Mallophaga, for example, Trichodectes spp. and Damalinea spp. From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix,* Pemphigus spp., *Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,*

Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.

From the order of the Arachnida, for example, *Scorpio maurus, Latrodectus mactans.*

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp., Tetranychus spp.

The phytoparasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp., Trichodorus spp.

The active compounds according to the invention in particular have outstanding activity against the caterpillars of the diamond-back moth (*Plutella maculipennis*).

The active compounds can be converted to the customary formulations, such as solutions, emulsions, wettable powders, suspensions, powders, dusting agents, pastes, soluble powders, granules, suspension emulsion concentrates, natural and synthetic materials impregnated with active compound and very fine capsules in polymeric substances.

These formulations are produced in a known manner, for example by mixing the active compounds with extenders, that is liquid solvents and/or solid carriers, if appropriate with the use of surfactants, that is emulsifiers and/or dispersing agents and/or foam-forming agents.

If the extender used is water, it is also possible to employ, for example, organic solvents as auxiliary solvents. Suitable liquid solvents are essentially: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol and also their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are:

for example ammonium salts and ground natural minerals, such as kaolins, clays, talc, chalk, quartz, attapulgite, montmorillonite or diatomaceous earth, and ground synthetic minerals, such as highly disperse silica, alumina and silicates; suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifying and/or foam-forming agents are: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysis products; suitable dispersing agents are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, and also natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compound according to the invention can be present in its commercially available formulations and in the use forms, prepared from these formulations, as a mixture with other active compounds, such as insecticides, attractants, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

Examples of particularly advantageous mixing components are the following:

Fungicides:

2-aminobutane; 2-anilino-4-methyl-6-cyclopropyl-pyrimidine; 2',6'-dibromo-2-methyl-4'-trifluoromethoxy-4 '-trifluoro-methyl-1,3-thiazole-5-carboxanilide; 2,6-dichloro-N-(4-trifluoromethylbenzyl)-benzamide; (E)-2-methoxyimino-N-methyl-2-(2-phenoxyphenyl)-acetamide; 8-hydroxyquinoline sulphate; methyl (E)-2-{2-[6-(2-cyanophenoxy)-pyrimidin-4-yloxy]-phenyl}-3-methoxyacrylate; methyl (E)-methoximino[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezine, dicloran, diethofencarb, difenoconazole, dimethirimol, dimethomorph, diniconazole, dinocap, diphenylamine, dipyrithione, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, phthalide, pimaricin, piperalin, polycarbamate, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole, valida-mycin A, vinclozolin, zineb, ziram.

Bactencides:

bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

Insecticides/Acaricides/Nematicides:

abamectin, AC 303 630, acephate, acrinathrin, alanycarb, aldicarb, alphamethrin, amitraz, avermectin, AZ 60541, azadirachtin, azinphos A, azinphos M, azocyclotin, Bacillus thuringiensis, bendiocarb, benfuracarb, bensultap, beta-cyfluthrin, bifenthrin, BPMC, brofenprox, bromophos A, bufencarb, buprofezin, butocarboxin, butylpyridaben, cadusafos, carbaryl, carbofuran, carbophenothion, carbosulfan, cartap, CGA 157419, CGA 184699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mevinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemeton M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozine, pyrachlophos, pyradaphenthion, pyresmethrin, pyrethrum, pyridaben, pyrimidifen, pyriproxifen, quinalphos, RH 5992, salithion, sebufos, silafluofen, sulfotep, sulprofos, tebufenozide, tebufenpyrad, tebupirimphos, teflubenzuron, tefluthrin, temephos, terbam, terbufos, tetrachlorvinphos, thiafenox, thiodicarb, thiofanox, thiomethon, thionazin, thuringiensin, tralomethrin, triarathene, triazophos, triazuron, trichlorfon, triflumuron, trimethacarb, vamidothion, XMC, xylylcarb, YI 5301/5302, zetamethrin.

A mixture with other known active compounds, such as herbicides, or with fertilizers and growth-regulators is also possible.

The active compound according to the invention can furthermore be present in its commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms. When used against hygiene pests and pests of stored products, the active compound has an excellent residual action on wood and clay as well as a good stability to alkali on limed substrates.

Furthermore, it has been found that the compounds of the formula (I) according to the invention have a potent insecticidal action against insects which destroy industrial materials.

The following insects may be mentioned by way of preferred examples but without any limitation:

Beetles, such as *Hylotrupes bajulus, Chlorophorus pilosis, Anobium punctatum, Xestobium rufovillosum, Ptilinus pecticomis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis,* Xyleborus spec. Tryptodendron spec. *Apate monachus, Bostrychus capucins, Heterobostrychus brunneus,* Sinoxylon spec. *Dinoderus minutus*

Dermapterans, such as *Sirex juvencus, Urocerus gigas, Urocerus gigas taignus* and *Urocerus augur.*

Termites, such as *Kalotermes flavicollis, Cryptotermes brevis, Heterotermes indicola, Reticulitermes flavipes, Reticulitermes santonensis, Reticuliternes lucifugus, Mastotermes darwiniensis, Zootermopsis nevadensis* and *Coptotermes formosanus.*

Bristletails, such as *Lepisma saccharina.*

Industrial materials are to be understood as meaning, in the present context, non-live materials, such as, preferably, synthetic materials, glues, sizes, paper and board, leather, wood and timber products, and paint.

The materials to be very particularly preferably protected against attack by insects are wood and timber products.

Wood and timber products which can be protected by the composition according to the invention or mixtures comprising such a composition are to be understood as meaning, for example: construction timber, wooden beams, railway sleepers, bridge components, jetties, wooden vehicles, boxes, pallets, containers, telephone poles, wood lagging, windows and doors made of wood, plywood, particle board, joiner's articles, or wood products which, quite generally, are used in the construction of houses or in joinery.

The active compounds can be used as such, in the form of concentrates or generally customary formulations, such as powders, granules, solutions, suspensions, emulsions or pastes.

The formulations mentioned can be prepared in a manner known per se, for example by mixing the active compounds with at least one solvent or diluent, emulsifier, dispersant and/or binder or fixative, water repellent, if appropriate desiccants and UV stabilizers and, if appropriate, colorants and pigments and other processing auxiliaries.

The insecticidal compositions or concentrates used for the protection of wood and wooden materials comprise the active compound according to the invention at a concentration of 0.0001 to 95% by weight, in particular 0.001 to 60% by weight.

The amount of the compositions or concentrates employed depends on the species and the occurrence of the insects and on the medium. The optimum rate of application can be determined upon use in each case by test series. However, in general, it suffices to employ 0.0001 to 20% by weight, preferably 0.001 to 10% by weight, of the active compound, based on the material to be protected.

The solvent and/or diluent used is an organochemical solvent or solvent mixture and/or an oily or oil-type organochemical solvent or solvent mixture of low volatility and/or a polar organochemical solvent or solvent mixture and/or water and, if appropriate, an emulsifier and/or wetting agent.

Organochemical solvents which are preferably employed are oily or oil-like solvents having an evaporation number of above 35 and a flashpoint of above 30° C., preferably above 45° C. Substances which are used as such oily and oil-like solvents which have low volatility and are insoluble in water are suitable mineral oils or their aromatic fractions, or mineral-oil-containing solvent mixtures, preferably white spirit, petroleum and/or alkylbenzene.

Substances which are advantageously used are mineral oils with a boiling range of 170 to 220° C., white spirit with a boiling range of 170 to 220° C., spindle oil with a boiling range of 250 to 350° C., petroleum or aromatics of boiling range 160 to 280° C., essence of turpentine and the like.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably α-monochloronaphthalene, are used.

The organic oily or oil-like solvents of low volatility and having an evaporation number of above 35 and a flashpoint of above 30° C., preferably above 45° C., can be partially replaced by organochemical solvents of high or medium volatility, with the proviso that the solvent mixture also has an evaporation number of above 35 and a flashpoint of above 30° C., preferably above 45° C., and that the insecticide/fungicide mixture is soluble or emulsifiable in this solvent mixture.

In a preferred embodiment, part of the organochemical solvent or solvent mixture is replaced or an aliphatic polar organochemical solvent or solvent mixture. Substances which are preferably used are aliphatic organochemical solvents having hydroxyl and/or ester and/or ether groups, such as, for example, glycol ether, esters and the like.

The organochemical binders used within the scope of the present invention are the synthetic resins and/or binding drying oils which are known per se and can be diluted with water and/or are soluble or dispersible or emulsifiable in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin, such as indene/coumarone resin, silicone resin, drying vegetable and/or drying oils and/or physically drying binders based on a natural and/or synthetic resin.

The synthetic resin used as the binder can be employed in the form of an emulsion, dispersion or solution. Up to 10% by weight of bitumen or bituminous substances can also be used as binder. In addition, colorants, pigments, water repellents, odour-masking substances and inhibitors or anti-corrosives known per se and the like can also be employed.

The composition or the concentrate preferably comprises, in accordance with the invention, at least one alkyd resin or modified alkyd resin and/or a drying vegetable oil as the organochemical binder. Preferably used according to the invention are alkyd resins with an oil content of over 45% by weight, preferably 50 to 68% by weight.

All or some of the abovementioned binder can be replaced by a fixative (mixture) or a plasticizer (mixture). These additives are intended to prevent volatilization of the active compounds and crystallization or precipitation. They preferably replace 0.01 to 30% of the binder (based on 100% of binder employed).

The plasticizers are from the chemical classes of the phthalic esters, such as dibutyl phthalate, dioctyl phthalate or benzylbutyl phthalate, the phosphoric esters, such as tributyl phosphate, the adipic esters, such as di-(2-ethylhexyl)adipate, the stearates, such as butyl stearate or amyl stearate, the oleates, such as butyl oleate, the glycerol ethers or relatively high-molecular-weight glycol ethers, glycerol esters and p-toluenesulphonic esters.

Fixatives are chemically based on polyvinyl alkyl ethers, such as, for example, polyvinyl methyl ether, or ketones, such as benzophenone or ethylenebenzophenone.

Particularly suitable as a solvent or diluent is also water, if appropriate as a mixture with one or more of the above-mentioned organochemical solvents or diluents, emulsifiers and dispersants.

Particularly effective protection of wood is achieved by large-scale industrial impregnation processes, for example vacuum, double-vacuum or pressure processes.

If appropriate, the ready-to-use compositions can additionally comprise other insecticides and, if appropriate, additionally one or more fungicides.

Suitable additional components which may be admixed are, preferably, the insecticides and fungicides mentioned in WO 94/29 268. The compounds mentioned in that document are expressly incorporated into the present application.

Very particularly preferred components which may be admixed are insecticides, such as chlorpyriphos, phoxim, silafluofin, alphamethrin, cyfluthrin, cypermethrin, deltamethrin, permethrin, imidacloprid, NI-25, flufenoxuron, hexaflumuron and triflumuron, and fungicides, such as epoxyconazole, hexaconazole, azaconazole, propiconazole, tebuconazole, cyproconazole, metconazole, imazalil, dichlorfluanid, tolylfluanid, 3-iodo- 2-propinyl-butyl carbamate, N-octyl-isothiazolin-3-one and 4,5-dichloro-N-octylisothiazolin-3-one.

The preparation and the use of the active compounds according to the invention can be seen from the examples which follow.

PREPARATION EXAMPLES

Example I-1

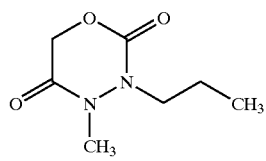
(Process A)

At 0° C., 5.49 g of ethyldiisopropylamine and subsequently, a little at a time, 5.19 g of bis-(2-oxo-3-oxazolidinyl)-phosphoryl chloride were added to a solution of 3.0 g (2-methyl-1-propylhydrazyl)-carbonyloxy-acetic acid (for example from Ex. II-1) in 750 ml of dry dichloromethane. The mixture was stirred at 0° C. for 2 h and then allowed to warm to room temperature overnight. The solution was concentrated and the residue was taken up in 300 ml of ethyl acetate. The solution was washed with semisaturated NH$_4$Cl solution and saturated NaCl solution and dried with sodium sulphate. The drying agent was filtered off, the solution was concentrated and the product was purified by column chromatography (stationary phase: silica gel; mobile phase cyclohexane:ethyl acetate=2:1). This gave 1.70 g (71% of theory) of 3-propyl-4-methyl-1,3,4-oxadianane-2,5-dione as a yellow-brown oil.

$^1$H NMR (500 MHz, CDCl$_3$) δ [ppm]: 0.97 (t, 3H, CH$_2$CH$_3$); 1.62 (sx, 2H, CH$_2$CH$_2$); 3.23 (s, 3H, NCH$_3$); 3.68 (t, 2H, NH$_2$); 4.59 (s, 2H, OCH$_2$).

Examples I-2 to I-15

Similar to Example I-1, the compounds of the formula (I-j) listed in Table 1 below were obtained.

TABLE 1

(I-j)

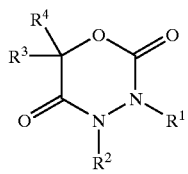

$R^2$ = CH$_3$   $R^4$ = H

| Ex. No. | R$^1$ | R$^3$ | Physical data: M.p. o. $^1$H—NMR (CDCl$_3$): δ [ppm] |
|---|---|---|---|
| I-2 | CH$_2$CH(CH$_3$)$_2$ | H | 75–77° C. |
| I-3 | (CH$_2$)$_3$CH$_3$ | H | 27–28° C. |
| I-4 | CH$_2$(CH$_3$)$_2$ | H | 45–47° C. |
| I-5 | C$_6$H$_5$-CH$_2$ | H | 82–83° C. |
| I-6 | CH$_3$ | H | 41–43° C. |
| I-7 | cyclopropyl-CH$_2$ | H | 0.71 (q 2H); 0.73 (q 2H); 1.05 (m 1H); 3.25 (s 3H); 3.58 (d 2H); 4.62 (s 2H) |
| I-8 | Br-C$_6$H$_4$-CH$_2$ | H | 66–69° C. |
| I-9 | H$_3$C-CH(CH$_3$)-(CH$_2$)$_3$-CH(CH$_3$)-CH$_2$ | H | 30–32° C. |
| I-10 | (CH$_3$)$_3$CCH$_2$ | H | 92–93° C. |
| I-11 | CH$_2$CH(CH$_3$)$_2$ | C$_6$H$_5$-CH$_2$ | 70–71° C. |
| I-12 | CH$_2$CH(CH$_3$)$_2$ | CH$_3$ | 66–67° C. |

TABLE 1-continued

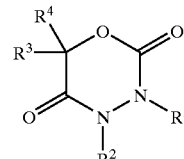

(I-j)

$R^2 = CH_3$  $R^4 = H$

| Ex. No. | $R^1$ | $R^3$ | Physical data: M.p. o. $^1$H—NMR (CDCl$_3$): δ [ppm] |
|---|---|---|---|
| I-13 | 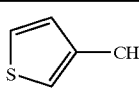 | H | 86–88° C. |
| I-14 | 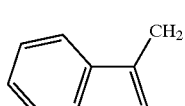 | H | 156–158° C. |
| I-15 | 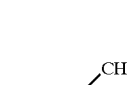 | H | 70–72° C. |

Example I-16

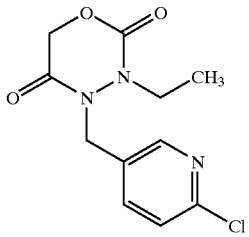

Similar to Example I-1, 5.0 g of [2-(2-chloro-5-pyridyl)-methyl-1-ethylhydrazyl)-carbonyloxy-acetic acid (for example from Example I-16) gave 3.33 g (79% of theory) of 4-(2-chloro-5-pyridylmethyl)-3-ethyl-1,3,4-oxadiazine-2,5-dione of melting point 125–128° C.

Example II-1

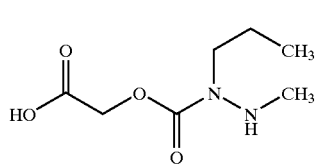

(Process A.a)

4.36 g of benzyl (2-methyl-1-propylhydrazyl)-carbonyloxy-acetate (for example from Example III-1) were dissolved in 100 ml of ethyl acetate. 100 mg of Pd/C (10%) were added as catalyst and the reaction solution was hydrogenated at an H$_2$ pressure of 1 bar. After the reaction had ended, nitrogen was passed through the solution and the solution was subsequently freed from catalyst by filtration through diatomaceous earth (Celite®). Concentration under reduced pressure gave 3.0 g (100% of theory) of (2-methyl-1-propylhydrazyl)-carbonyloxy-acetic acid as a brown, viscous oil. The crude product was reacted further according to Example 1-1 without any purification.

$^1$H NMR (500 MHz, CDCl$_3$) δ [ppm]: 0.90 (t, 3H, CH$_2$CH$_3$); 1.65 (m, 2H CH$_2$CH$_3$); 2.65 (br s, 3H; NCH$_3$); 3.37 (t, 2H, NCH$_2$); 4.68 (br s, 2H, OCH$_2$); 6.65 (br s, 2H, NH, CO$_2$H).

Examples II-2 to II-12

Similar to Example II-1, the compounds of the formula (II) listed in Table 2 below were obtained.

TABLE 2

(II)

Structure: HO-C(=O)-C(R³)(R⁴)-O-C(=Q¹)-N(R¹)-N(H)(R²)

$R^2 = CH_3$   $R^4 = H$   $Q^1 = O$

| Ex. No. | R¹ | R³ | Physical data: ¹H—NMR (CDCl₃): δ [ppm] |
|---|---|---|---|
| II-2 | CH₂CH(CH₃)₂ | H | 0.90 (s 2H); 2.05 (m 1H); 2.63 (br s 3H); 3.22 (d 2H); 4.68 (br s 2H) |
| II-3 | (CH₂)₃CH₃ | H | |
| II-4 | CH₂(CH₃)₂ | H | 1.17 (d 6H); 2.64 (br s 3H); 4.28 (m 1H); 4.69 (s 2H); 6.0 (br s 2H) |
| II-5 | C₆H₅-CH₂ | | 2.55 (br s 3H); 4.63 (s 2H); 4.71 (s 2H); 6.76 (br s 2H); 7.30 (m 5H) |
| II-6 | CH₃ | H | 2.63 (br s 3H); 3.12 (br s 3H); 3.90 (br s 2H); 4.69 (s 2H) |
| II-7 | cyclopropyl-CH₂ | H | 0.30 (m 2H); 0.50 (m 2H); 1.13 (br m 1H); 2.668 (br s 3H); 3.32 (d 2H); 4.70 (br s 2H) |
| II-8 | 4-Br-C₆H₄-CH₂ | H | 2.60 (br s 3H); 3.20 (br s 2H); 4.75 (s 2H); 7.35 (m 4H) |
| II-9 | (CH₃)₂CH(CH₂)₃CH(CH₃)CH₂ | H | 0.85 (2d 9H); 1.05–1.70 (ms 10H); 2.63 (br s 3H); 3.42 (t 2H); 4.67 (s 2H); 5.40 (br s 2H) |
| II-10 | (CH₃)₃CCH₂ | H | 0.95 (s 9H); 2.60 (br s 3H); 3.20 (s 2H); 4.0 (br 2H); 4.68 (br s 2H) |
| II-11 | CH₂CH(CH₃)₂ | C₆H₅-CH₂ | 0.80 (m 6H); 1.90 (br m 1H); 2.50 (br s 3H); 3.10 (m 4H); 4.0 (br 2H); 7.28 (m 5H) |
| II-12 | CH₂CH(CH₃)₂ | CH₃ | 0.95 (m 9H); 1.55 (m 1H); 2.80 (br s 3H); 3.35 (m 2H); 5.10 (m 1H); 5.75 (br s, 2H) |

Example II-13

(Process A.a/b)

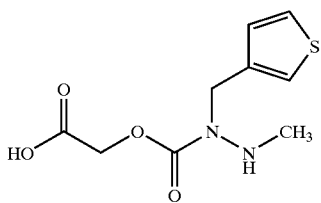

At 0° C., 50.5 g of trifluoroacetic acid were added dropwise to a solution of 10 g of tertbutyl [2-tert-butoxycarbonyl-2-methyl-1-(3-thienylmethyl)-hydrazyl]-carbonyloxy-acetate (for example from Example IV-13) in 100 ml of dry dichloromethane. After 2 h, the mixture was allowed to warm to room temperature and the completeness of the reaction was checked by TLC (silica gel, cyclohexane:ethyl acetate=2:1). Under reduced pressure, the solution, with added dichloromethane, was repeatedly concentrated to remove the acid (ultimately at high vacuum). This gave 12.56 g of 2-methyl-1-(3-thienylmethyl)-hydrazyl-carbonyloxy-acetic acid as a brown, viscous oil. The crude product was reacted further according to Example I-13 without purification.

¹H NMR (500 MHz, CDCl₃) δ [ppm]: 2.83 (br s, 3H NCH₃); 4.80 and 4.90 (2s, 2×2H, NCH₂, OCH₂); 7.10 (m, 1H, arom); 7.35 (m, 1H, arom); 7.40 (m, 1H, arom.); 7.63 (br s, 2H, NH, CO₂H).

Example II-14

(Process A.a/b)

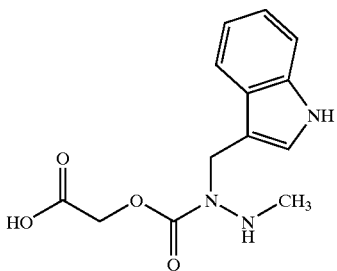

2.5 g of benzyl [2-benzyloxycarbonyl-2-methyl-1-(3-indolylmethyl)-hydrazyl]-carbonyloxy-acetate (for example from Ex. IV-14) were dissolved in 30 ml of ethanol. 50 mg of Pd/C (10%) were added as catalyst, and the reaction solution was then hydrogenated using an $H_2$ pressure of 1 bar. After the reaction had ended, nitrogen was passed through the solution which was subsequently freed from the catalyst by filtration through diatomaceous earth (Celite®). The mixture was concentrated under reduced pressure, giving 1.3 g (95% of theory) of [1-(3indoly)-2-methyl-hydrazyl]-carbonyloxy acetic acid of melting point 50–53° C. The crude product was reacted further according to Example I-14 without purification.

$^1$H NMR (500 MHz, CDCl$_3$) δ [ppm]: 2.65 (br s, 3H, NCH$_3$); 4.80 (2s, 4H, OCH$_2$, NCH$_2$); 7.0–8.2 (m, 6H, NH, arom).

Example II-15

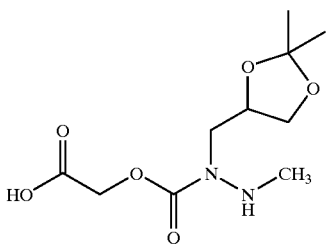

By the method of Example II-14, benzyl [2-benzyloxycarbonyl-2-methyl-1-(2,2-dimethyl-1,3-dioxo-4-yl)-methyl-2-methyl-hydrazyl]-carbonyloxy-acetate (for example from Example IV-15) gave [1-(2,2-dimethyl-1,3-dioxo-4-yl)-methyl-2-methyl-hydrazyl]-carbonyloxy-acetic acid.

$^1$H NMR (500 MHz, CDCl$_3$) δ [ppm]: 1.35 u. 1.43 (2s, 2×3H, C(CH$_3$)$_2$); 2.63 (br s, 3H, NCH$_3$); 3.60 (br m, 2H, NCH$_2$); 3.84 (br m, 1H, OCHCH$_2$); 4.08 u. 4.37 (2 br m, 2×1H, OCH$_2$CH); 4.68 (br m, 2H, CO—CH$_2$O); 6.0 (br s, 2H, NH, CO$_2$H).

Example II-16

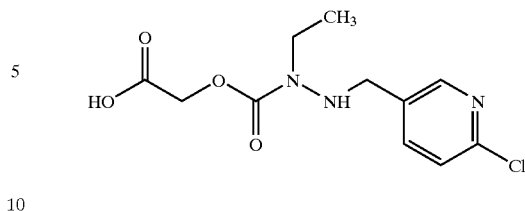

By the method of Example II-13, 7.52 g of tert-butyl [2-tert-butoxycarbonyl-2-(2-chloro-5-pyridyl)-methyl-1-ethyl-hydrazyl]-carbonyloxy-acetate (for example from Example IV-16) gave 4.9 g (100% of theory) of [2-(2-chloro-5-pyridyl)-methyl-1-ethylhydrazyl]-carbonyloxy-acetic acid.

$^1$H NMR (500 MHz, CDCl$_3$) δ [ppm]: 1.10 (br t, 3H, CH$_2$CH$_3$); 3.30 (br s, 2H, NCH$_2$); 4.10 (br s, 2H, NCH$_2$); 4.72 (s, 2H, OCH$_2$); 7.43/17.89/8.38 (3 m, 3×1H, arom).

Example III-1

(Process A.a.b)

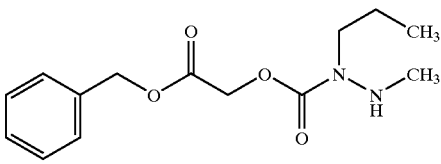

At 0° C., 16.9 g of trifluoroacetic acid were added dropwise to a solution of 6.65 g of benzyl (2-tert-butoxycarbonyl-2-methyl-1-propylhydrazyl)-carbonyloxy-acetate (for example from Ex. IV-1) in 50 ml of dry dichloromethane. The solution was stirred at 0° C. for 2 to 3 h and allowed to warm to RT overnight. The reaction solution was concentrated under reduced pressure. The residue was taken up in 300 ml of ethyl acetate and washed with saturated sodium bicarbonate and saturated sodium chloride solution. The organic phase was dried over sodium sulphate, the drying agent was filtered off and the filtrate was concentrated under reduced pressure. This gave 4.76 g (100% of theory) of benzyl (2-methyl-1-propylhydrazyl)-carbonyloxy-acetate as a brown viscous oil. The crude product was reacted further according to Example II-1 without purification.

$^1$H NMR (500 MHz, CDCl$_3$) δ [ppm]: 0.88 (t, 3H, CH$_2$CH$_3$); 1.64 (sx, 2H, CH$_2$CH$_3$); 2.60 (br s, 3H, NCH$_3$); 3.35 (t, 2H, CH$_2$CH$_3$); 4.69 (br s, 2H, CH$_2$Ph); 5.20 (OCH$_2$), 7.37 (m, 5H, arom.).

Examples III-2 to III-12

By the method of Example III-1, the compounds of the formula (X) listed in Table 3 below were obtained.

TABLE 3

(X)

Structure: A²-O-C(=O)-C(R³)(R⁴)-O-C(=Q¹)-N(R¹)-N(H)-R²

A² = benzyl, R² = CH₃, R⁴ = H, Q¹ = O

| Ex. No. | R¹ | R³ | Physical data: $^1$H—NMR (CDCl$_3$): δ [ppm] |
|---|---|---|---|
| III-2 | CH$_2$CH(CH$_3$)$_2$ | H | 0.88 (d 6H); 1.55 (br s 1H); 2.03 (sp 1H); 2.60 (br s 3H); 3.20 (d 2H); 4.70 (m 2H); 5.20 (s 2H); 7.35 (m 5H) |
| III-3 | (CH$_2$)$_3$CH$_3$ | H | 0.92 (t 3H); 1.30 (m 2H); 1.58 (qn 2H); 2.60 (br s 3H); 3.48 (t 2H); 4.70 (br s 2H); 5.20 (s 2H); 7.35 (m 5H) |
| III-4 | CH$_2$(CH$_3$)$_2$ | H | 1.15 (d 6H); 1.55 (br s 1H); 2.62 (br s 3H); 4.25 (br s 1H); 4.70 (s 2H); 5.19 (s 2H); 7.35 (m 5H) |
| III-5 | benzyl (PhCH$_2$) | H | 1.55 (br s 1H); 2.53 (br s 3H); 4.10 (s 2H); 4.24 (s 2H); 5.21 (s 2H); 7.30 (m 10H) |
| III-6 | CH$_3$ | H | 2.60 (br s 3H); 2.90 (br s 1H); 3.10 (br s 3H); 4.69 (s 2H); 5.20 (s 2H); 7.35 (m 5H) |
| III-7 | cyclopropyl-CH$_2$ | H | 0.28 (m 2H); 0.47 (m 2H); 1.12 (m 1H); 2.65 (br s 3H); 3.28 (d 2H); 4.70 (br s 2H); 5.20 (br s 2H); 7.35 (m 5H) |
| III-8 | 4-Br-C$_6$H$_4$-CH$_2$ | H | 2.54 (br s 3H); 4.30 (br s 1H); 4.53 (s 2H); 4.73 (s 2H); 5.22 (s 2H); 7.35 (m 9H) |
| III-9 | (CH$_3$)$_2$CH-CH$_2$-CH$_2$-CH(CH$_3$)-CH$_2$ | H | |
| III-10 | (CH$_3$)$_3$CCH$_2$ | H | 0.93 (s 9H); 2.57 (br s 3H); 3.19 (s 2H); 4.68 (br m 2H); 5.20 (s 2H); 7.35 (m 5H) |
| III-12 | CH$_2$CH(CH$_3$)$_2$ | CH$_3$ | 0.90 (2d 6H); 1.53 (d 3H); 2.70 (br s 3HH); 3.27 (m 2H); 5.18 (m 3H); 7.35 (m 5H) |

Example IV-1

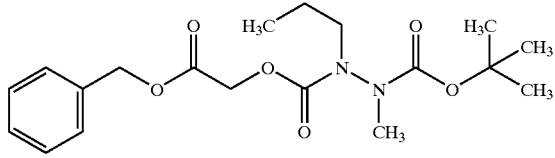

For about 1 h, carbon dioxide gas was introduced into a suspension of 22.80 g of caesium carbonate and 6.55 g of 1-tert-butoxycarbonyl-1-methyl-2-propyl-hydrazine in 140 ml of dry dimethylformamide. 8.02 g of benzyl bromoacetate were then slowly added in a dropwise fashion, and carbon dioxide was introduced for a further 30–45 min. The reaction mixture was stirred overnight and then poured into 300 ml of semisaturated sodium chloride solution and extracted with 3×150 ml of ethyl acetate. The organic phase was dried over sodium sulphate, the drying agent was filtered off and the filtrate was concentrated under reduced pressure at a temperature of not more than 50° C. The product was purified by column chromatography (silica gel; cyclohexane:ethyl acetate=5:1). This gave 8.9 g (67% of theory) of benzyl (2-tert-butoxycarbonyl-2-methyl-1-propylhydrazyl)-carbonyloxy-acetate as a light-yellow viscous oil.

$^1$H NMR (500 MHz, CDCl$_3$) δ [ppm]: 0.93 (t, 3H, CH$_2$CH$_3$); 1.47 (ms, 9H, C(CH$_3$)$_3$); 1.63 (m, 2H, CH$_2$CH$_3$); 2.90–3.55 (ms, 5H, NCH$_2$, NCH$_3$); 4.40–5.25 (ms, 4H, CH$_2$Ph, OCH$_2$); 7.36 (m, 5H, C$_5$H$_5$).

Example IV-2

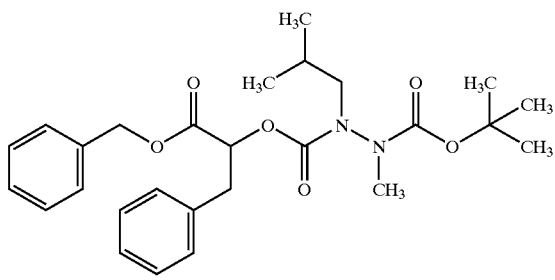

At 0–5° C., a solution of 25.63 g of benzyl D-phenyllactate and 11.13 g of triethylamine in 130 ml of dry tetrahydrofuran was added dropwise over a period of 1 h to a solution of 19.8 g of phosgene in 100 ml of toluene. The mixture was then stirred at 0° C. for about 30 min. and at room temperature for 1 h. Precipitated solid was filtered off and the solution was concentrated under reduced pressure. The resulting crude chloroformate was taken up in 50 ml of dry tetrahydrofuran and added dropwise over a period of 1–2 h to a solution of 20.24 g of 1-tert-butoxycarbonyl-1-methyl-2-sec-butyl-hydrazine and 10.12 g of triethylamine in 70 ml of dry tetrahydrofuran which had been cooled to 0° C. The mixture was subsequently allowed to warm to room temperature and stirred overnight. The reaction solution was added to 200 ml of semisaturated sodium chloride solution and extracted with 3×150 ml of ethyl acetate. The organic phase was dried over sodium sulphate, the drying agent was filtered off and the filtrate was concentrated under reduced pressure. The product was purified by column chromatography (silica gel; cyclohexane: ethyl acetate=10:1). This gave 36.83 g (76% of theory) of benzyl 1-(2-tert-butoxycarbonyl-2-methyl-1-sec-butyl-hydrazyl)-carbonyloxy-2-phenylpropionate as a light-yellow viscous oil.

$^1$H NMR (500 MHz, CDCl$_3$) δ [ppm]: 0.90 (ms, 6H, CH(C$\underline{H}_3$)$_2$); 1.30–1.75 (ms, 10H, CH(CH$_3$)$_2$, C(CH$_3$)$_3$); 2.60–3.40 (ms, 6H, OCH, NCH$_2$, NCH$_3$); 5.0–5.40 (ms, 4H, 2 CH$_2$Ph); 7.25 (m, 10H, 2 C$_6$H$_5$).

Examples IV-3 to IV-12

By the methods of Examples IV-1 and IV-2, the compounds of the formula (XII) listed in Table 4 below were obtained.

TABLE 4

(XII)

$A^2\text{—O—}\underset{\underset{R^3\ R^4}{}}{\text{C}}\text{(=O)—O—}\underset{\underset{Q^1}{\|}}{\text{C}}\text{—N(R}^1\text{)—N(A}^3\text{)—R}^2$

| | $A^2$ = benzyl | $A^3$ = BOC | $R^2$ = CH$_3$ | $R^4$ = H   $Q^1$ = O |
|---|---|---|---|---|
| Ex. No. | $R^1$ | | $R^3$ | Physical data: M.p. o. $^1$H—NMR (CDCl$_3$): δ [ppm] |
| IV-3 | CH$_2$CH(CH$_3$)$_2$ | | H | 0.95 (2d 6H); 1.45 (4s 9H); 1.95 (m 1H); 3.0–3.4 (ms 5H); 4.4–5.25 (ms 4H); 7.35 (m, 5H) |
| IV-4 | (CH$_2$)$_3$CH$_3$ | | H | 0.95 (m 3H); 1.30–1.60 (m 13H); 3.05–3.65 (m 5H); 4.4–5.3 (m 4H); 7.35 (m 5H) |
| IV-5 | CH$_2$(CH$_3$)$_2$ | | H | 1.20 (2d 6H); 1.45 (ms 9H); 3.08 (m 3H); 4.3–5.25 (ms 5H); 7.35 (m 5H) |
| IV-6 | C$_6$H$_5$—CH$_2$— | | H | 1.35–1.55 (ms 9H); 2.80 (ms 3H) 4.30–5.30 (ms 6H); 7.35 (ms 10H) |
| IV-7 | CH$_3$ | | H | 1.45 (ms 9H); 3.0–3.20 (ms 6H); 4.40–5.30 (ms 4H); 7.35 (ms 5H) |
| IV-8 | cyclopropyl-CH$_2$— | | H | 0.25 (m; 2H); 0.55 (m 2H); 1.05 (m 1H); 1.45 (ms 9H); 3.10–3.65 (ms 5H); 4.40–5.30 (ms 4H); 7.35 (m 5H) |
| IV-9 | 4-Br-C$_6$H$_4$—CH$_2$— | | H | 1.45 (ms 9H); 2.85 (ms 3H); 4.25–5.30 (ms 6H); 7.15–7.50 (m 9H) |
| IV-10 | H$_3$C—CH(CH$_3$)—(CH$_2$)$_3$—CH(CH$_3$)—CH$_2$— | | H | 0.88 (ms 9H); 1.05–1.70 (ms 19H); 3.07 (m 3H); 3.35–3.70 (m 2H); 4.40–5.30 (ms 4H); 7.35 (m 5H) |

TABLE 4-continued (XII)

$$A^2\text{—O—CO—C(R}^3)(R^4)\text{—O—C(Q}^1)\text{—N(R}^1)\text{—N(R}^2)(A^3)$$

| | $A^2$ = benzyl | $A^3$ = BOC | $R^2$ = $CH_3$ | $R^4$ = H | $Q^1$ = O |
|---|---|---|---|---|---|
| Ex. No. | $R^1$ | | $R^3$ | Physical data: M.p. o. $^1$H—NMR (CDCl$_3$): δ [ppm] | |
| IV-11 | $(CH_3)_3CCH_2$ | | H | 0.95 (s 9H); 1.45 (ms 9H); 3.0–3.5 (ms 5H); 4.35–5.25 (ms 4H); 7.35 (m 5H) | |
| IV-12 | $CH_2CH(CH_3)_2$ | | $CH_3$ | 0.9–1.15 (ms 6H); 1.50 (m 12H); 1.90 (m 1H); 3.0–3.45 (ms 5H); 5.0–5.25 (ms 3H); 7.45 (m 5H) | |

Example IV-13

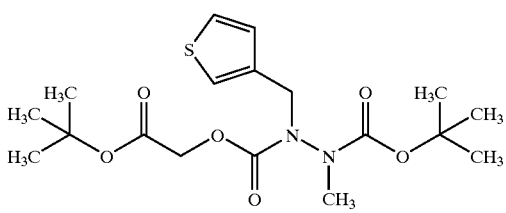

Carbon dioxide gas was introduced into a suspension of 22.80 g of caesium carbonate in 140 ml of dry dimethylformamide for about 20 min. Subsequently, 8.47 g of 1-tert-butoxycarbonyl-1-methyl-2-(3-thienylmethyl)-hydrazine were slowly added dropwise. Carbon dioxide was introduced for a further 60 min., 6.83 g of tert-butyl bromoacetate were then slowly added dropwise and carbon dioxide was introduced for a further 30–45 min. The reaction mixture was stirred overnight and then added to 200 ml of semisaturated sodium chloride solution and extracted with 3×150 ml of ethyl acetate. The organic phase was dried over sodium sulphate, the drying agent was filtered off and the filtrate was concentrated under reduced pressure at a temperature of not more than 50° C. The product was purified by column chromatography (silica gel; cyclohexane: ethyl acetate=5:1). This gave 14.1 g (100% of theory) of tert-butyl-[2-tert-butoxycarbonyl-2-methyl-1-(3-thienylmethyl)-hydrazyl]-carbonyloxy-acetate.

$^1$H NMR (500 MHz, CDCl$_3$) δ [ppm]: 1.35–1.55 (m, 18H, 2×C(CH$_3$)$_3$); 2.87 (m, 3H, NCH$_3$); 4.25–5.05 (ms, 4H, OCH$_2$, NCH$_2$); 7.20 (m, 3H, arom.).

Example IV-14

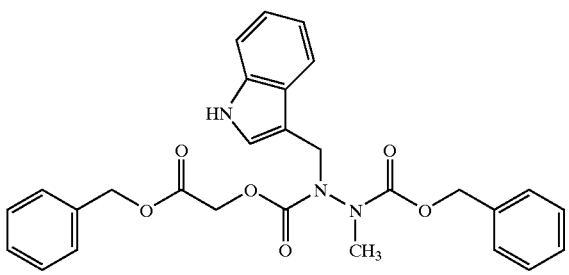

By the method of Example IV-1, 10.8 g of 1-benzyloxycarbonyl-1-methyl-2-(3-indolylmethyl)-hydrazine and 8.02 g of benzyl bromoacetate gave, in three fractions, 6.41 g of pure and 7.04 g of slightly impure (76% of theory) benzyl [2-benzyloxy-carbonyl-2-methyl-1-(3-indolylmethyl)-hydrazyl]-carbonyloxy-acetate.

$^1$H NMR (500 MHz, CDCl$_3$) δ [ppm]: 2.83 (m, 3H, NCH$_3$); 4.10–5.35 (ms 6H, NH$_2$, OCH$_2$, CH$_2$Ph); 7.35 (m, 15H, arom); 8.05 (br s, 1H, NH).

Example IV-15

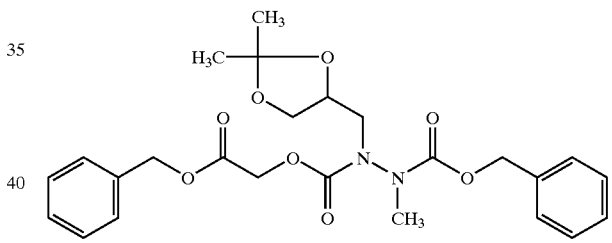

By the method of Example IV-1, 1-benzyloxycarbonyl-1-methyl-2-(2,2-dimethyl-1,3dioxo-4-yl)-methyl-hydrazine and benzyl bromoacetate gave benzyl [2-benzyloxy-carbonyl-2-methyl-1-(2,2-dimethyl-1,3-dioxo-4-yl)-methyl-2-methyl-hydrazyl]-carbonyloxy-acetate.

$^1$H NMR (500 MHz, CDCl$_3$) δ [ppm]: 1.23 to 1.43 (m, 6H, C(CH$_3$)$_2$; 3.12–3.20 (m 3H, NCH$_3$); 3.25–4.97 (m, 7H, OCH$_2$, NCH$_2$, NCH$_2$C<u>H</u>, OCHC<u>H</u>$_2$O); 5.17 (m, 4H, 2×CH$_2$Ph); 7.35 (m, 1H, arom).

Example IV-16

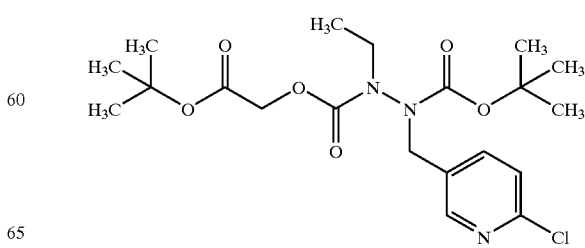

By the method of Example IV-13, 7.13 g of 1-tert-butoxycarbonyl-1-(2-chloro-5-pyridyl)-methyl-2-ethyl-hydrazine and 4.87 g of tert-butyl bromoacetate gave 955 g (86% of theory) of tert-butyl [2tert-butoxycarbonyl-2-(2chloro-5-pyridyl)-methyl-1-ethylhydrazyl]-carbonyloxy-acetate.

$^1$H NMR (500 MHz, CDCl$_3$): 1.0 (m, 3H, C$\underline{H}_3$CH$_2$); 1.47 (ms, 18H, 2×C(CH$_3$)$_3$); 3.15–3.45 (ms, 2H, NCH$_2$); 4.05–5.0 (ms, 4H, NCH$_2$, OCH$_2$); 7.30/7.75/8.40 (3m, 3×1H, arom).

USE EXAMPLES

Example A

*Haemonchus Contortus*/sheep

Sheep experimentally infected with *Haemonchus contortus* were treated after expiry of the prepatency time of the parasite.

The active compounds were administered orally in gelatin capsules as pure active compound.

The efficacy is determined by quantitatively counting the nematode eggs excreted with the faeces before and after treatment.

Complete cessation of oviposition after treatment means that the nematodes have been expelled or are so damaged that they no longer produce eggs (effective dose).

The following results were obtained:

| Active compound Example No. | effective dose in mg/kg |
| --- | --- |
| I-2 | 5 |
| I-3 | 5 |
| I-11 | 5 |

Example B

Plutella test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and populated with caterpillars of the diamond-back moth (*Plutella maculipennis*) while the leaves are still moist.

After the desired period of time, the kill in % is determined 100% means that all the caterpillars have been killed; 0% means that none of the caterpillars have been killed.

In this test, for example the compound of Preparation Example I-2 exhibited, at an exemplary active compound concentration of 0.1%, a kill of 100% after 7 days.

What is claimed is:
1. A carbazate having the Formula (II)

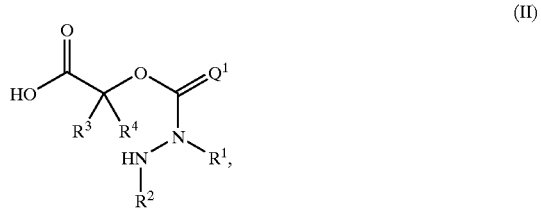

in which
R$^1$ and R$^2$ independently of one another each represent hydrogen, respectively optionally halogen-substituted alkyl, hydroxyalkyl, alkanoyloxyalkyl, alkoxyalkyl, arylalkoxyalkyl, mercaptoalkyl, alkylthioalkyl, alkyl-sulphinyl-alkyl, alkylsulphonylalkyl, carboxyalkyl, alkoxycarbonylalkyl, aryloxycarbonylalkyl, arylalkyloxycarbonylalkyl, carbamoylalkyl, amino-alkyl, alkylaminoalkyl, dialkylaminoalkyl, alkoxycarbonyl-aminoalkyl, alkylcarbonyl, cycloalkylcarbonyl or represent respectively optionally substituted cycloalkyl, cycloalkylalkyl, aryl, arylalkyl, arylcarbonyl, heterocyclylalkyl, hetaryl or hetarylalkyl or R$^1$, R$^2$ and the two linking nitrogen atoms represent an optionally substituted heterocyclic ring, R$^3$ and R$^4$ independently of one another each represent hydrogen, respectively optionally halogen-substituted alkyl, alkenyl, hydroxyalkyl, alkanoyloxyalkyl, alkoxyalkyl, arylalkoxyalkyl, mercaptoalkyl, alkylthioalkyl, alkyl-sulphinyl-alkyl, alkylsulphonylalkyl, alkoxycarbonylalkyl, aryloxycarbonylalkyl, arylalkyloxycarbonylalkyl, carbamoylalkyl, amino-alkyl, alkylaminoalkyl, dialkylaminoalkyl, alkylcarbonyl, cycloalkylcarbonyl or represent respectively optionally substituted cycloalkyl, cycloalkylalkyl, aryl, arylalkyl, hetaryl or hetarylalkyl or R$^3$ and R$^4$ together represent alkylene or the radical (a)

in which
R$^5$ and R$^6$ independently of one another each represent hydrogen, respectively optionally halogen-substituted alkyl, alkenyl, hydroxyalkyl, alkanoyloxyalkyl, alkoxyalkyl, arylalkoxyalkyl, mercaptoalkyl, alkylthioalkyl, alkylsulphinylalkyl, alkylsulphonylalkyl, alkoxycarbonylalkyl, aryloxycarbonylalkyl, aminoalkyl, alkylaminoalkyl, dialkylaminoalkyl, alkylcarbonyl or represent respectively optionally substituted cycloalkyl, cycloalkylalkyl, aryl, arylalkyl, hetaryl or hetarylalkyl and Q$^1$ represents oxygen or sulphur, with the exception of the compounds of the Formula (II) in which simultaneously R$^2$ and R$^4$ each represent hydrogen, R$^1$ represents hydrogen or C$_1$–C$_5$-alkyl and R$^3$ represents methyl or benzyl and with the further exception of the compounds of the Formula (II) in which R$^1$ represents methyl, R$^2$ represents phenylcarbonyl, $R^3$ represents methyl or phenyl, $R^4$ represents hydrogen and $Q^1$ represents oxygen.

2. A process for preparing the carbazate of the Formula (II) according to claim 1, comprising the step of
a) cleaving off a protective group $A^2$ from a C-terminal protected carbazate of the Formula (X)

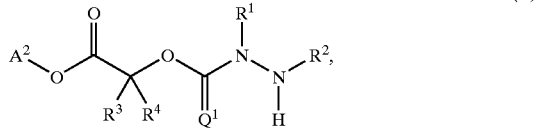
(X)

in which
$R^1, R^2, R^3, R_4$ and $Q^1$ are each as defined in claim 1 and $A^2$ represents a C-terminal protective group,
with the exception of the compounds of Formula (X) wherein $R^2$ and $R^4$ each represent hydrogen, $R^1$ represents C1–C5-alkyl and $R^3$ represents methyl or benzyl and
with the further exception of the compounds of the Formula (X) in which $R^1$ represents methyl, $R^2$ represents hydrogen or phenylcarbonyl, $R^3$ represents phenyl, $R^4$ represents hydrogen, $A^2$ represents tert.-butyl and
$Q^1$ represents oxygen and
with the further exception of the compounds of the Formula (X) in which
$R^1$ represents methyl, $R^2$ represents phenylcarbonyl, $R^3$ represents methyl,
$R^4$ represents hydrogen, $A^2$ represents benzyl and $Q^1$ represents oxygen or
b) cleaving off a protective group $A^3$ from an N-terminal protected carbazate of the Formula (XI)

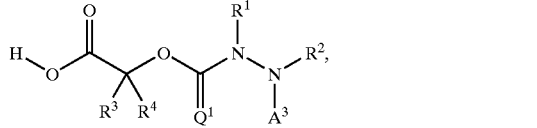
(XI)

in which
$R^1, R^2, R^3, R^4$ and $Q^1$ are each as defined in claim 1 and $A^3$ represents an N-terminal protective group.

3. A C-terminal protected carbazate having the Formula (X)

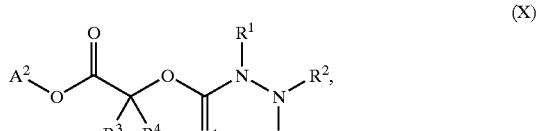
(X)

in which
$R^1, R^2, R^3, R^4$ and $Q^1$ are each as defined in claim 1 and $A^2$ represents a C-terminal protective group,
with the exception of the compounds of Formula (X) in which $R^2$ and $R^4$ each represent hydrogen, $R^1$ represents $C_1$–$C_5$-alkyl and $R^3$ represents methyl or benzyl and
with the further exception of the compounds of the Formula (X) in which $R^1$ represents methyl, $R^2$ represents hydrogen or phenylcarbonyl, $R^3$ represents phenyl, $R^4$ represents hydrogen, $A^2$ represents tert-butyl and $Q^1$ represents oxygen and
with the further exception of the compounds of the Formula (X) in which $R^1$ represents methyl, $R^2$ represents phenylcarbonyl, $R^3$ represents methyl, $R^4$ represents hydrogen, $A^2$ represents benzyl and $Q^1$ represents oxygen.

4. A process for preparing the C-terminal protected carbazate having the Formula (X) according to claim 3, comprising the step of:
a) cleaving off an N-terminal protective group $A^3$ from an N- and C-terminal protected carbazate of the Formula (XII)

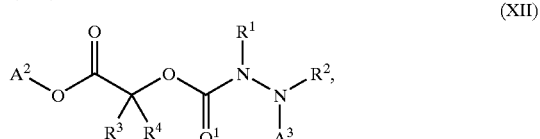
(XII)

in which
$R^1, R^2, R^3, R^4, Q^1$ and $A^2$ are each as defined in claim 3 and $A^3$ represents an N-terminal protective group.

5. An N- and C-terminal protected carbazate of the Formula

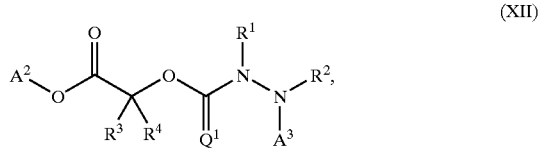
(XII)

in which
$R^1, R^2, R^3, R^4, Q^1$ and $A^2$ are each as defined in claim 3 and $A^3$ represents an N-terminal protective group,
with the exception of the compounds of the Formula (XII) in which $R^2$ and $R^4$ each represent hydrogen, $R^1$ represents $C_{1-5}$-alkyl and $R^3$ represents methyl or benzyl.

6. A process for preparing the N- and C-terminal protected carbazate of the Formula (XII) according to claim 5 with the exception of the compounds of the Formula (XII) in which $R^2$ and $R^4$ each represent hydrogen, $R^1$ represents $C_1$–$C_5$-alkyl and $R^3$ represents methyl or benzyl, comprising the step of:
reacting a compound of the Formula (XIII)

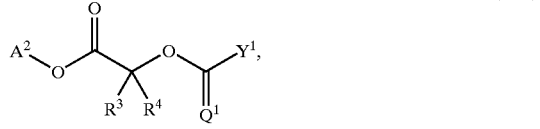
(XIII)

in which
$A^2, R^3, R^4$ and $Q^1$ are each as defined in claim 3,
$Y^1$ represents halogen, trichloromethoxy, $C_1$–$C_4$-alkoxy, 1-imidazolyl or 1,2,4-triazolyl,
with a hydrazine of the Formula (XIV)

(XIV)

in which
$R^1$ and $R^2$ are each as defined in claim 3 and $A^3$ represents an N-terminal protective group.

* * * * *